(12) United States Patent
Yu et al.

(10) Patent No.: US 12,245,857 B2
(45) Date of Patent: Mar. 11, 2025

(54) DUAL-HELMET MAGNETOENCEPHALOGRAPHY APPARATUS

(71) Applicant: KOREA RESEARCH INSTITUTE OF STANDARDS AND SCIENCE, Daejeon (KR)

(72) Inventors: Kwon-Kyu Yu, Daejeon (KR); Yong-Ho Lee, Daejeon (KR); Hyukchan Kwon, Daejeon (KR); Jin-Mok Kim, Daejeon (KR); Sang-Kil Lee, Daejeon (KR); Bokyung Kim, Daejeon (KR); Min-Young Kim, Daejeon (KR); Kiwong Kim, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 136 days.

(21) Appl. No.: 17/853,769

(22) Filed: Jun. 29, 2022

(65) Prior Publication Data
US 2022/0330869 A1    Oct. 20, 2022

Related U.S. Application Data

(63) Continuation of application No. PCT/KR2021/002437, filed on Feb. 26, 2021.

(30) Foreign Application Priority Data

Jun. 1, 2020    (KR) .................. 10-2020-0066113

(51) Int. Cl.
*A61B 5/245*    (2021.01)
*A61B 5/00*    (2006.01)
(Continued)

(52) U.S. Cl.
CPC ............ *A61B 5/245* (2021.01); *A61B 5/6803* (2013.01); *G01R 33/0076* (2013.01);
(Continued)

(58) Field of Classification Search
CPC ..... A61B 5/245; A61B 5/4064; A61B 5/6803; A61B 562/0223; A61B 2562/066; G01R 33/326
See application file for complete search history.

(56) References Cited

U.S. PATENT DOCUMENTS 5,713,354 A * 2/1998 Warden .................. A61B 5/245
                                                600/409
9,823,312 B2   11/2017 Yu et al.
(Continued)

FOREIGN PATENT DOCUMENTS

CN    104620123 A    5/2015
CN    110891482 A    3/2020
(Continued)

OTHER PUBLICATIONS

International Search Report & Written Opinion dated Jun. 9, 2021; International Patent Application No. PCT/KR2021/002437; 10 pgs.; Korean Intellectual Property Office, Daejeon, Republic of Korea.
(Continued)

*Primary Examiner* — John D Li
(74) *Attorney, Agent, or Firm* — Andrew D. Fortney; Central California IP Group, P.C.

(57) ABSTRACT

A dual-helmet magnetoencephalography measuring apparatus includes: an internal container storing a liquid refrigerant; an external container disposed to surround the internal container and including a first external helmet and a second external helmet disposed to be spaced apart from each other; a first sensor-mounted helmet disposed to surround the first external helmet between the external container and the
(Continued)

internal container; a second sensor-mounted helmet disposed to surround the second external helmet between the externa container and the internal container; a plurality of first SQUID sensor module disposed on the first sensor-mounted helmet; and a plurality of second SQUID sensor module disposed on the second sensor-mounted helmet.

32 Claims, 16 Drawing Sheets

(51) Int. Cl.
  *G01R 33/00* (2006.01)
  *G01R 33/035* (2006.01)
(52) U.S. Cl.
  CPC .. *G01R 33/0354* (2013.01); *A61B 2562/0223* (2013.01); *A61B 2562/046* (2013.01); *A61B 2562/18* (2013.01)

(56) References Cited

U.S. PATENT DOCUMENTS

| | | | |
|---|---|---|---|
| 10,585,151 B2 | 3/2020 | Yu et al. | |
| 11,766,204 B2 | 9/2023 | Burton et al. | |
| 2007/0144207 A1* | 6/2007 | Klotten | F25B 43/006 |
| | | | 62/503 |
| 2009/0145909 A1* | 6/2009 | Hausberger | F17C 3/00 |
| | | | 220/500 |
| 2012/0252678 A1* | 10/2012 | Kim | G01R 33/326 |
| | | | 62/51.1 |
| 2013/0090241 A1* | 4/2013 | Harrison | H01F 6/04 |
| | | | 324/322 |
| 2015/0268311 A1* | 9/2015 | Yu | G01R 1/18 |
| | | | 505/162 |
| 2016/0223622 A1 | 8/2016 | Yu et al. | |
| 2017/0067969 A1 | 3/2017 | Butters et al. | |
| 2017/0168121 A1* | 6/2017 | Yu | A61B 5/05 |
| 2020/0196887 A1* | 6/2020 | Burton | A61B 5/369 |
| 2022/0330870 A1* | 10/2022 | Yu | A61B 5/6803 |

FOREIGN PATENT DOCUMENTS

| | | |
|---|---|---|
| KR | 101007498 B1 | 1/2011 |
| KR | 20140054638 A | 5/2014 |
| KR | 20150047680 A | 5/2015 |
| KR | 20160031349 A | 3/2016 |

OTHER PUBLICATIONS

Office Action dated Jul. 15, 2024; Chinese Patent Application No. 202180010493.5; 14 pgs.; China Intellectual Property Administration, Beijing, China.

* cited by examiner

DUAL-HELMET MAGNETOENCEPHALOGRAPHY APPARATUS

CROSS-REFERENCE TO RELATED APPLICATIONS

This application is a continuation of and claims priority to PCT/KR2021/002437 filed on Feb. 26, 2021, which claims priority to Korea Patent Application No. KR 10-2020-0066113 filed on Jun. 1, 2020, the entireties of which are both hereby incorporated by reference.

TECHNICAL FIELD

The present disclosure relates to a magnetoencephalography apparatus and, more particularly, to a magnetoencephalography apparatus provide with dual helmets.

BACKGROUND

A magnetoencephalography apparatus is an apparatus for measuring magnetic signals generated by microcurrent of cerebral neural circuits, and is used to study brain functions and to diagnose functional brain diseases.

In general, a magnetoencephalography signal has an amplitude of 10 fT to 1 pT and has a frequency of 0.1 to 1 kHz. Accordingly, there is a requirement for a magnetic sensor having improved sensitivity and a technology to cancel environmental magnetic noise. At present, a magnetic sensor which is most advantageous in practical terms is a superconducting quantum interference device (SQUID) based on a low-temperature superconductor niobium (Nb).

Since Nb used for a low-temperature superconducting SQUID has a critical temperature of 9 K, cooling using liquid helium or a low-temperature freezer is required. Current magnetoencephalography apparatuses need to supplement liquid helium. Optimization of a structure, a thickness, and an installing method of a material is required to reduce thermal magnetic noise, caused by a superinsultion and thermal shield installed in a Dewar vacuum portion, while reducing an evaporation rate of a Dewar. In addition, since helium gas tends to easily pass through a small gap, high density of glass fiber reinforced plastics, used as a material of the Dewar, is required.

Since the intensity of a magnetic signal from a magnetic field signal source decreases in inverse proportion to the square of a distance, a distance between the signal source and a pick-up coil needs to be significantly reduced to increase a signal-to-noise ratio (SNR). Research into such a method has been conducted to develop and use a coil-in-vacuum (CIV) SQUID in which a pick-up coil is disposed in a vacuum vessel.

In a CIV SQUID apparatus, a pick-up coil and a SQUID sensor are disposed to be maintained in a vacuum state. Accordingly, only a low-temperature refrigerant is present in an internal helium storage container for storing a liquid refrigerant. Accordingly, there is only a path to fill the refrigerant. Accordingly, a diameter of a neck portion of the internal helium storage container may be significantly reduced. As a result, an evaporation rate of the liquid refrigerant may be reduced.

SUMMARY

An aspect of the present disclosure is to provide a coil-in-vacuum and dual-helmet structure, capable of measuring both adults and children in a single magnetoencephalography apparatus measuring device.

Another aspect of the present disclosure is to provide a cooling apparatus having a dual-wall structure, capable of blocking radiant heat.

Another aspect of the present disclosure is to provide a coolant tube structure having a coaxial dual-tube structure, capable of providing a rotational motion of a Dewar.

Another aspect of the present disclosure is to provide a cooling device, capable of recycling a refrigerant.

Another aspect of the present disclosure is to provide a magnetoencephalography measuring apparatus including two helmets.

A dual-helmet magnetoencephalography measuring apparatus according to an example embodiment includes: an internal container storing a liquid refrigerant; an external container disposed to surround the internal container and including a first external helmet and a second external helmet disposed to be spaced apart from each other; a first sensor-mounted helmet disposed to surround the first external helmet between the external container and the internal container; a second sensor-mounted helmet disposed to surround the second external helmet between the external container and the internal container; a plurality of first SQUID sensor module disposed on the first sensor-mounted helmet; and a plurality of second SQUID sensor module disposed on the second sensor-mounted helmet. A space between the external container and the internal container is in a vacuum state.

In an example embodiment, the external container may branch off in the form of T. The external container may include a first branch and a second branch branching off from a cylindrical external container body portion in the form of T. Each of the first external helmet and the second external helmet may be coupled to the first branch and the second branch, respectively. The first external helmet and the second external helmet may face each other and may have different sizes.

In an example embodiment, the dual-helmet magnetoencephalography measuring apparatus may further include: a rotational motion unit rotating the internal container and the external container about a central axis of the rotational motion unit.

In an example embodiment, the internal container may include: a neck portion into which a baffle insert is inserted; and an internal body portion having an increased diameter as compared with the neck portion. The neck portion may have a double-wall structure including an internal cylinder and an external cylinder surrounding the internal cylinder.

In an example embodiment, the neck portion may further include a heat shielding layer disposed between the internal cylinder and the external cylinder.

In an example embodiment, the internal cylinder may further include a plurality of ring projections protruding outwardly of the internal cylinder. Thermal anchors may be coupled to the ring projections, respectively. The ring projections may be disposed to be spaced apart from each other. The external cylinder may be separated with the ring projection interposed therebetween.

In an example embodiment, an external circumferential surface of the ring projection and an internal circumferential surface of the thermal anchor may be screw-coupled to each other.

In an example embodiment, the thermal anchor may include a cylindrical thermal anchor coupling portion and a disc-shaped thermal anchor body portion disposed on an external circumferential surface of the thermal anchor coupling portion. An internal circumferential surface of the thermal anchor coupling portion may be screw-coupled to an external circumferential surface of the ring projection.

In an example embodiment, the internal container may include: a neck portion into which a baffle insert is inserted; and a body portion having a diameter increased as compared to the neck portion. The dual-helmet magnetoencephalography measuring apparatus may further include: a refrigerant exhaust tube disposed at the baffle insert and exhausting an evaporated refrigerant; a refrigerant injection tube disposed at the baffle insert and injecting a refrigerant; and a condenser connected to the refrigerant exhaust tube and the refrigerant injection tube and condensing an evaporated refrigerant exhausted through the refrigerant injection tube. The refrigerant injection tube may have a coaxial structure inserted into the refrigerant exhaust tube.

In an example embodiment, each of the refrigerant exhaust tube and the refrigerant injection tube may be a dual tube including an internal tube and an external tube.

In an example embodiment, the dual-helmet magnetoencephalography measuring apparatus may further include: a C-shaped external container support portion supporting lower surfaces of the first branch and the second branch; and a rotational motion unit coupled to the external container support portion to provide a rotational motion to the external container.

In an example embodiment, the dual-helmet magnetoencephalography measuring apparatus may further include: a vacuum-sealing portion inserted into a through-hole formed in the lower surface of each of the first and second branches to seal signal lines and disposed inside the external container support portion; and a signal line connection box disposed below the external container support portion and connecting the signal lines, sealed through the vacuum-sealing portion, to each other. The rotational motion unit may further include: an upper base box disposed to surround the signal line connection box; a lower base box disposed below the upper base box; and a bearing portion disposed between the upper base box and the lower base box to provide a rotational motion to the upper base box.

In an example embodiment, the dual-helmet magnetoencephalography measuring apparatus may further include: a handle coupled to an external side of the upper base box.

In an example embodiment, the first external helmet may include a coupled portion provided with a long groove. The first external helmet may be coupled to one end of the first branch while rotating along the long groove in an aligned state. The second external helmet may include a coupled portion provided with a long grove. The second external helmet may be coupled to one end of the second branch while rotating along the long groove in an aligned state.

In an example embodiment, the internal container may include: a neck portion into which a baffle insert is inserted; a first body portion having an increased diameter as compared with the neck portion; a second body portion having an increased diameter as compared with the first body portion; and a third body portion having a decreased diameter as compared with the second body portion.

In an example embodiment, the dual-helmet magnetoencephalography measuring apparatus may further include: a pair of first support portions coupled to an interface between the neck portion and the first body portion and respectively extending in a direction of the first external helmet and a direction of the second external helmet; a pair of second support portion coupled to an interface between the first body portion and the second body portion and respectively extending in the direction of the first external helmet and the direction of the second external helmet; a pair of third support portion coupled to an interface between the second body portion and the third body portion and respectively extending in the direction of the first external helmet and the direction of the second external helmet; a first fixing ring coupled to the first, second, and third support portions in the direction of the first external helmet; a second fixing ring coupled to the first, second, and third support portion in the direction of the second external helmet; a first auxiliary fixing part connecting the first fixing ring and the first sensor-mounted helmet; and a second auxiliary fixing part connecting the second fixing ring and the second sensomounted helmet.

In an example embodiment, each of the first, second, and third support portions may include a plurality of arc long grooves. A coupling member may be inserted into each of the arc long grooves to be coupled to the internal container.

In an example embodiment, the first sensor-mounted helmet may include: a helmet body having an open region for securing a view; a lower brim disposed along an edge of a lower surface of the helmet body; an upper brim providing a brim in the open portion of the helmet body; a helmet fixing ring having a ring shape at a predetermined interval from the lower brim and continuously connected to the upper brim; and a plurality of connection pillars vertically connecting the lower brim and the upper brim to each other.

In an example embodiment, the dual-helmet magnetoencephalography measuring apparatus may further include: a first auxiliary thermal anchor disposed on a lower surface of each of the upper brim and the lower brim of the first sensor-mounted helmet; a first internal 4K heat shielding portion being in thermal contact with the first auxiliary thermal anchor and disposed on an internal side surface of the first sensor-mounted helmet; and a first external 4K heat shielding portion being in thermal contact with the first auxiliary thermal anchor and disposed on an external side surface of the first sensor-mounted helmet. The first auxiliary thermal anchor, the first internal 4K heat shielding portion, and the first external 4K heat shielding portion may be in thermal contact with a main thermal anchor by a litz wire.

In an example embodiment, each of the plurality of first SQUID sensor modules may be in thermal contact with a main thermal anchor disposed on a lower surface of the internal container through a litz wire. Each of the plurality of second SQUID sensor modules may be in thermal contact with the main thermal anchor disposed on the lower surface of the internal container through a litz wire.

In an example embodiment, the first SQUID sensor modules may be cooled by a plural of litz wires. Some of the plurality of litz wires may be connected to first SQUID sensor modules arranged around the first SQUID sensor module, and the remainder of the plurality of litz wires may be in thermal contact with a main thermal anchor.

In an example embodiment, the first SQUID sensor module may be cooled by six litz wires. Among the six litz wires, two litz wires may be in thermal contact with the main thermal anchor, and four litz wires may be connected to the first SQUID sensor modules arranged around the first SQUID sensor module.

In an example embodiment, the internal container may include a neck portion into which a baffle insert is inserted. The neck portion may have a double-wall structure. Washershaped first to third thermal anchors, disposed to be vertically spaced apart from each other, may be provided on an external side of the neck portion. The first thermal anchor may be connected to a 120K heat shielding layer. The second thermal anchor may be connected to an 80K heat shielding layer. The third thermal anchor may be connected to a 40K heat shielding layer.

In an example embodiment, the 40K heat shielding layer may be disposed to surround the first sensor-mounted helmet and the second sensor-mounted helmet.

In an example embodiment, the first SQUID sensor module may be inserted into a through-hole, formed in the first sensor-mounted helmet, to be fixed. The first SQUID sensor module may include a plurality of holes. Litz wires may be respectively inserted into the holes to cool a SQUID sensor.

In an example embodiment, the main thermal anchor may include: a first heat transfer unit formed of oxygen-free copper and including a first disc, a first upper projection protruding from a central axis of the first disc to an upper surface of the first disc, and a first lower projection protruding from the central axis of the first disc to a lower surface of the first disc; a second heat transfer unit formed of oxygen-free copper and including a second disc, a second upper projection protruding from a central axis of the second disc to an upper surface of the second disc, and a second lower projection protruding from the central axis of the second disc to a lower surface of the second disc; a third heat transfer unit formed of oxygen-free copper and including a third disc, a third upper projection protruding from a central axis of the third disc to an upper surface of the third disc, and a third lower projection protruding from the central axis of the third disc to a lower surface of the third disc; a fourth heat transfer unit formed of oxygen-free copper and including a fourth disc, a fourth upper projection protruding from a central axis of the fourth disc to an upper surface of the fourth disc, and a fourth lower projection protruding from the central axis of the fourth disc to a lower surface of the fourth disc; a fifth heat transfer unit, formed of oxygen-free copper, coupled to the fourth heat transfer unit and having a strip shape; a first thermal expansion control unit formed of an insulating material and inserted between the first disc of the first heat transfer unit and the second disc of the second heat transfer; and a second thermal expansion control unit formed of an insulating material and inserted between the third disc of the third heat transfer unit and the fourth disc of the fourth heat transfer unit. The second upper projection of the second heat transfer unit may be provided with a groove for coupling to the first lower projection of the first heat transfer unit. The second lower projection of the second heat transfer unit may be provided with a groove for coupling to the third upper projection of the third heat transfer unit. The third lower projection of the third heat transfer unit may be provided with a groove for coupling to the fourth upper projection of the fourth heat transfer unit.

In an example embodiment, the first thermal expansion control unit may include: a first insulating body portion having the same diameter as a first diameter of the first disc; a second insulating body portion embedded in a lower surface of the internal container and having a second diameter greater than the first diameter; and a third insulating body portion having a third diameter smaller than the second diameter. The third insulating body portion may be disposed to surround an external circumferential surface of the second disc.

A magnetic field measuring apparatus according to an example embodiment includes: an external container; and a cylindrical internal container storing a liquid refrigerant and inserted into the external container. The internal container includes: a neck portion into which a baffle insert is inserted; and a body portion having an increased diameter as compared with the neck portion. The neck portion may have a double-wall structure including an internal cylinder and an external cylinder surrounding the internal cylinder.

In an example embodiment, the internal cylinder may further include a plurality of ring projections protruding outwardly of a cylinder. Thermal anchors may be coupled to the ring projections, respectively. The ring projections may be disposed to be spaced apart from each other. The external cylinder may be separated with the ring projection interposed therebetween.

In an example embodiment, the neck portion may further include a heat shielding layer disposed between the internal cylinder and the external cylinder.

In an example embodiment, an external circumferential surface of the ring projection and an internal circumferential surface of the thermal anchor may be screw-coupled to each other.

In an example embodiment, each of the thermal anchors may include a disc-shaped thermal anchor body portion disposed on both a cylindrical thermal anchor coupling portion and on an external circumferential surface of the thermal anchor coupling portion. An internal circumferential surface of the thermal anchor coupling portion may be screw-coupled to an external circumferential surface of the ring projection.

In an example embodiment, the thermal anchors may include first to third thermal anchors. The first thermal anchor may be connected to a 120K heat shielding layer, the second thermal anchor may be connected to an 80K heat shielding layer, and the third thermal anchor may be connected to a 40K heat shielding layer.

In an example embodiment, the magnetic field measuring apparatus may further include: a refrigerant exhaust tube disposed at the baffle insert and exhausting an evaporate refrigerant; a refrigerant injection tube disposed at the baffle insert and injecting a refrigerant; and a condenser connected to the refrigerant exhaust tube and the refrigerant injection tube and condensing an evaporated refrigerant exhausted through the refrigerant injection tube. The refrigerant injection tube may provide a coaxial structure to be inserted into the refrigerant exhaust tube. Each of the refrigerant exhaust tube and the refrigerant injection tube may be a dual tube including an internal tube and an external tube.

A magnetic field measuring apparatus according to an example embodiment include: an external container; a cylindrical internal container storing a liquid refrigerant and inserted into the external container; a baffle inserted into the internal container; a refrigerant exhaust tube disposed at the baffle insert and exhausting an evaporated refrigerant; a refrigerant injection tube disposed at the baffle insert and injecting a refrigerant; and a condenser connected to the refrigerant exhaust tube and the refrigerant injection tube and condensing an evaporate refrigerant exhausted through the refrigerant injection tube. The refrigerant injection tube may have a coaxial structure inserted into the refrigerant exhaust tube. Each of the refrigerant exhaust tube and the refrigerant injection tube may be a dual tube including an internal tube and an external tube.

In an example embodiment, the internal container may include: a neck portion where the baffle is inserted; and a body portion having an increased diameter as compared with the neck portion. The neck portion may have a double-wall structure including an internal cylinder and an external cylinder surrounding the internal cylinder.

A magnetic field measuring apparatus according to an example embodiment include: an external container; a cylindrical internal container storing a liquid refrigerant and inserted into the external container; a main thermal anchor disposed on a lower surface of the internal container; and a plurality of first SQUID sensor modules disposed on an external side of the internal container. Each of the plurality of first SQUID sensor modules may be in thermal contact with a main thermal anchor, disposed on a lower surface of the internal container, through a litz wire.

In an example embodiment, the main thermal anchor may include: a first heat transfer unit formed of oxygen-free copper and including a first disc, and a first lower projection protruding from the central axis of the first disc to a lower surface of the first disc; a second heat transfer unit formed of oxygen-free copper and including a second disc, a second upper projection protruding from a central axis of the second disc to an upper surface of the second disc, and a second lower projection protruding from the central axis of the second disc to a lower surface of the second disc; a third heat transfer unit formed of oxygen-free copper and including a third disc, a third upper projection protruding from a central axis of the third disc to an upper surface of the third disc, and a third lower projection protruding from the central axis of the third disc to a lower surface of the third disc; a fourth heat transfer unit formed of oxygen-free copper and including a fourth disc, a fourth upper projection protruding from a central axis of the fourth disc to an upper surface of the fourth disc; a first thermal expansion control unit formed of an insulating material and inserted between the first disc of the first heat transfer unit and the second disc of the second heat transfer; and a second thermal expansion control unit formed of an insulating material and inserted between the third disc of the third heat transfer unit and the fourth disc of the fourth heat transfer unit. The second upper projection of the second heat transfer unit may be provided with a groove for coupling to the first lower projection of the first heat transfer unit. The second lower projection of the second heat transfer unit may be provided with a groove for coupling to the third upper projection of the third heat transfer unit. The third lower projection of the third heat transfer unit may be provided with a groove for coupling to the fourth upper projection of the fourth heat transfer unit.

In an example embodiment, the first thermal expansion control unit may include: a first insulating body portion having the same diameter as a first diameter of the first disc; a second insulating body portion embedded in a lower surface of the internal container and having a second diameter greater than the first diameter; and a third insulating body portion having a third diameter smaller than the second diameter. The third insulating body portion may be disposed to surround an external circumferential surface of the second disc.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

Figure 1:
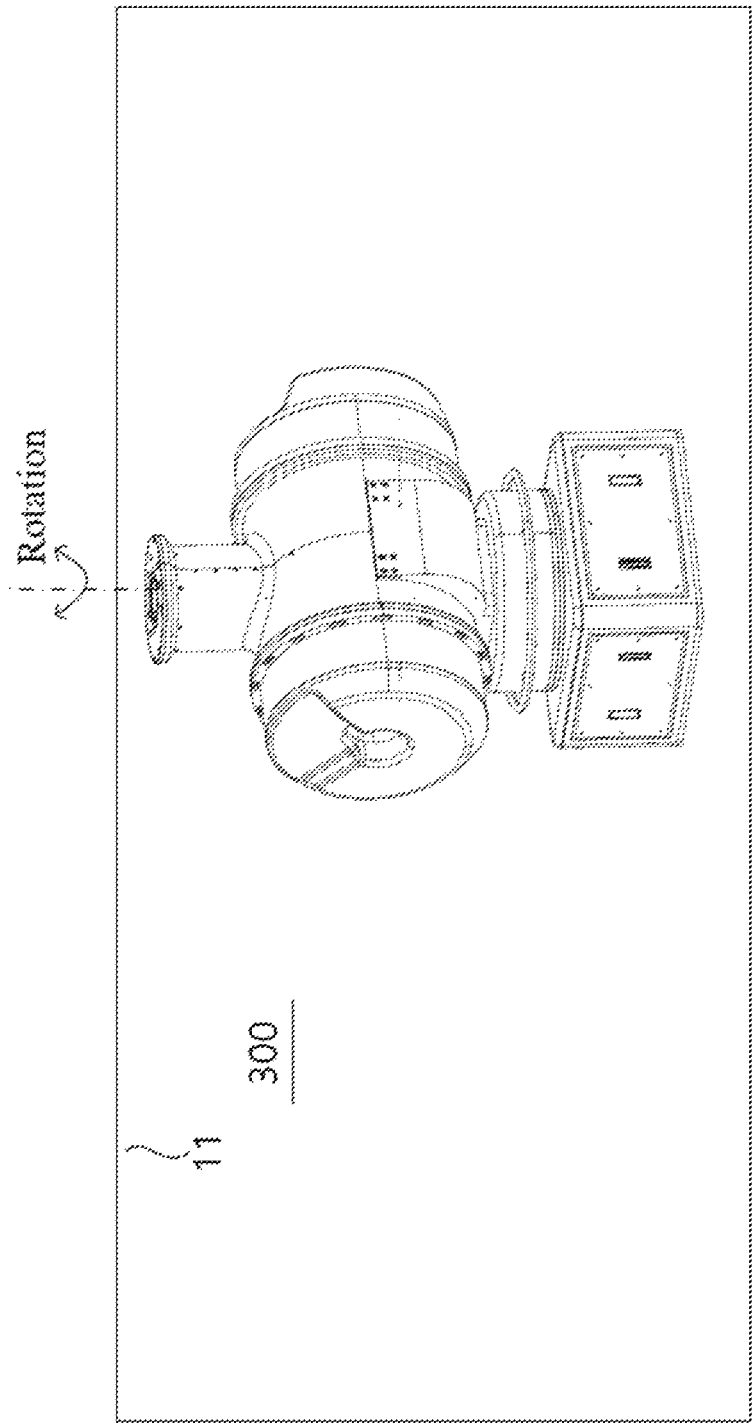
FIG. 1 is a conceptual diagram illustrating a magnetoencephalography measuring apparatus according to an example embodiment of the present disclosure.

According to an example embodiment, a technology for directly recondensing a helium gas using a refrigerator and resending the recondensed helium gas to a Dewar is applied. Since magnetic noise and vibration noise caused by the refrigerator and refrigerant delivery tube are significantly large, a special Dewar structure and a special SQUID arrangement method are required to prevent a SQUID from reacting with vibrations. In particular, a stable structure for supporting a SQUID-mounted helmet is required.

With the recent increase in the price of helium gas, a technology for directly recondensing a helium gas using a refrigerator and resending the recondensed helium gas to a magnetoencephalography Dewar is required. Vaporized helium is supplied to a refrigerator through a refrigerant exhaust tube, and a liquefied refrigerant is supplied to a Dewar through a refrigerant injection tube. When the refrigerant exhaust tube and the refrigerant injection tube include a single pipe, ice is condensed on a baffle insert lid. Such ice inhibits perfect sealing to causes lots of external heat influx.

A CIV SQUID according to an example embodiment addresses an issue regarding ice condensation on a baffle insert lid using a coaxial dual-tube structure. A refrigerant exhaust tube and a refrigerant injection tube have a coaxial structure, and each of the refrigerant exhaust tube and the refrigerant injection tube has a dual-tube structure. The dual-tube structure may prevent moisture condensation occurring on a surface of an upper plate of a Dewar. Accordingly, rotation of the Dewar may be provided using a sealing member such as an O-ring. In addition, the dual-tube structure may transfer a temperature of an evaporated helium gas to a cooler in a cold state, and thus, efficiency of the cooler may be improved.

In the CIV SQUID, the Dewar includes an internal container and an external container surrounding the internal container. However, the internal container absorbs radiant heat externally to increase consumption of a refrigerant.

In the CIV SQUID, the Dewar uses a double-wall structure in a neck portion of the internal container into which a baffle insert is inserted. Such a double-wall structure improves mechanical stability resulting from thermal expansion. In addition, a heat shielding layer disposed between the double walls reduces influx of radiant heat. In addition, a thermal anchor disposed on the outside of the double-wall structure uses a screw coupling to reduce damage caused by thermal expansion while being in thermal contact with an internal wall of the internal container having a double-wall structure through a large contact area. The double-wall structure may reduce an evaporation rate of the refrigerant and may stably support an internal structure with a high load, allowing internal vibration caused by evaporation of the refrigerant to be reduced.

A magnetoencephalography (MEG) signal depends on a distance between a SQUID sensor and a brain. Therefore, an MEG helmet for adults is not suitable to measure MEG of children. Accordingly, there is a need for a dual helmet in which a single MEG apparatus can measure both adults and children.

A helmet for children may be provided with 144 channels, and a helmet for adults may be provided with 192 channels. Therefore, as a structure optimal for a head size, it is expected that the quality of, in particular, children's MEG signals will be improved. It is advantageous to measure development processes of children's brain functions to adults' brain functions.

A magnetoencephalography apparatus according to an example embodiment has a structure in which two helmets are disposed on a single Dewar. A helmet for children and a helmet for adults, having different sizes, are mounted to face each other.

In a magnetoencephalography apparatus according to an example embodiment, each of a helmet for children and a helmet for adults may measure magnetoencephalography in a lying state according to a rotation state of a Dewar. To provide a rotational motion of the Dewar, a rotational motion unit may provide a rotation motion of the Dewar using a non-metallic bearing. The rotational motion unit may include a signal line connection box, to which signal lines are connected, therein.

A magnetoencephalography apparatus according to an example embodiment includes a main thermal anchor disposed on a lower surface of an internal container. The main thermal anchor includes a plurality of heat transfer portions, screw-coupled to each other, and a thermal expansion control portion formed of an insulating material and controlling sealing failure caused by thermal expansion between the heat transfer portion and the internal container. When the plurality of heat transfer portions are coupled to each other, a pair of thermal expansion control portions, disposed to be embedded in an external surface and an internal surface of the internal container, are pressed to inhibit damage to components caused by sealing and thermal expansion.

Hereinafter, embodiments of the present disclosure will be described below more fully with reference to accompanying drawings. The present disclosure may, however, be embodied in different forms and should not be constructed as limited to the embodiments set forth herein. Rather, these embodiments are provided so that this disclosure will be thorough and complete, and will fully convey the scope of the present invention to those skilled in the art.

FIG. 1 is a conceptual diagram illustrating a magnetoencephalography measuring apparatus according to an example embodiment of the present disclosure.

Figure 2:
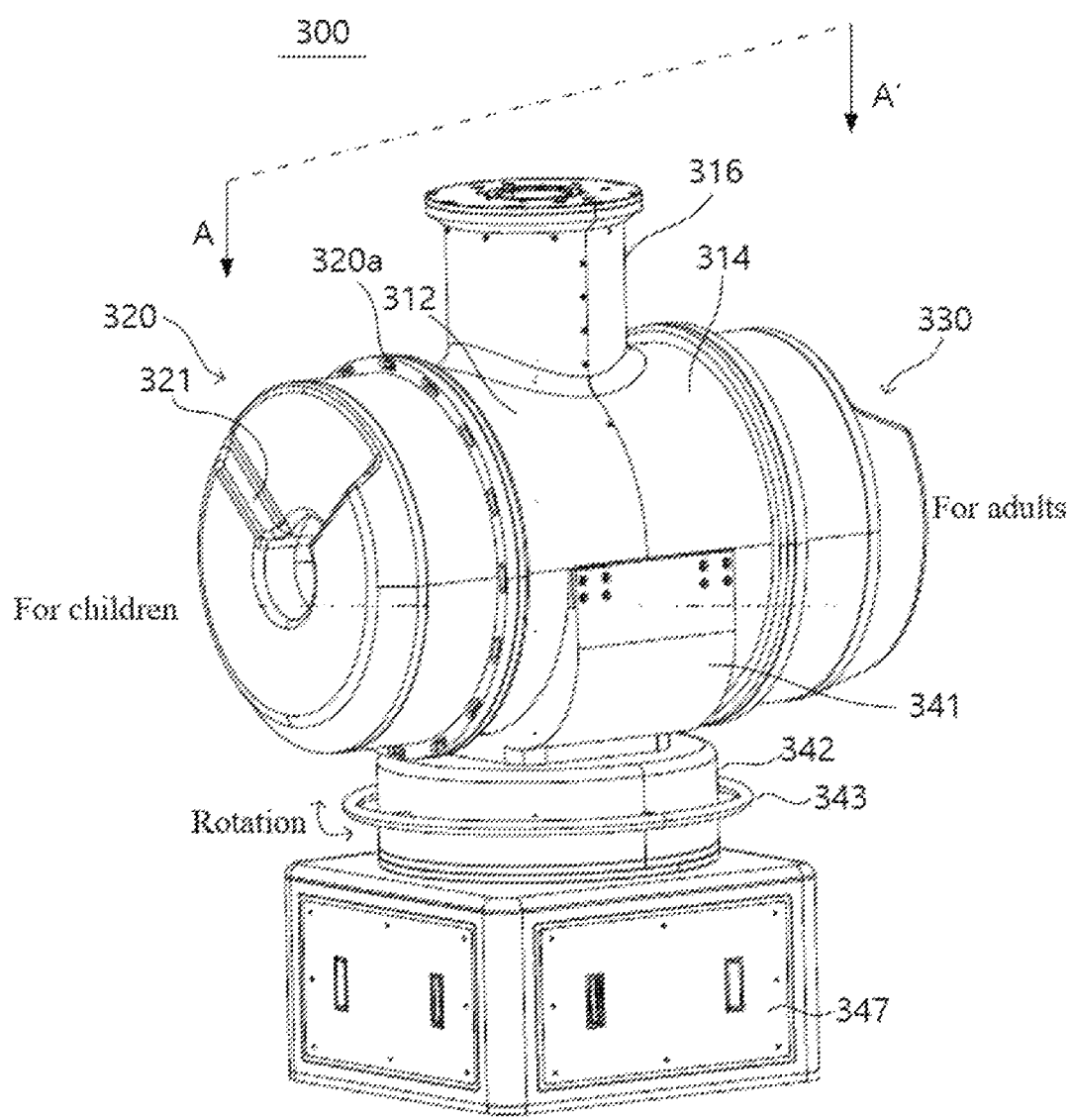
FIG. 2 is a perspective view illustrating a magnetoencephalography measuring apparatus.

FIG. 2 is a perspective view illustrating a magnetoencephalography measuring apparatus.

Figure 3:
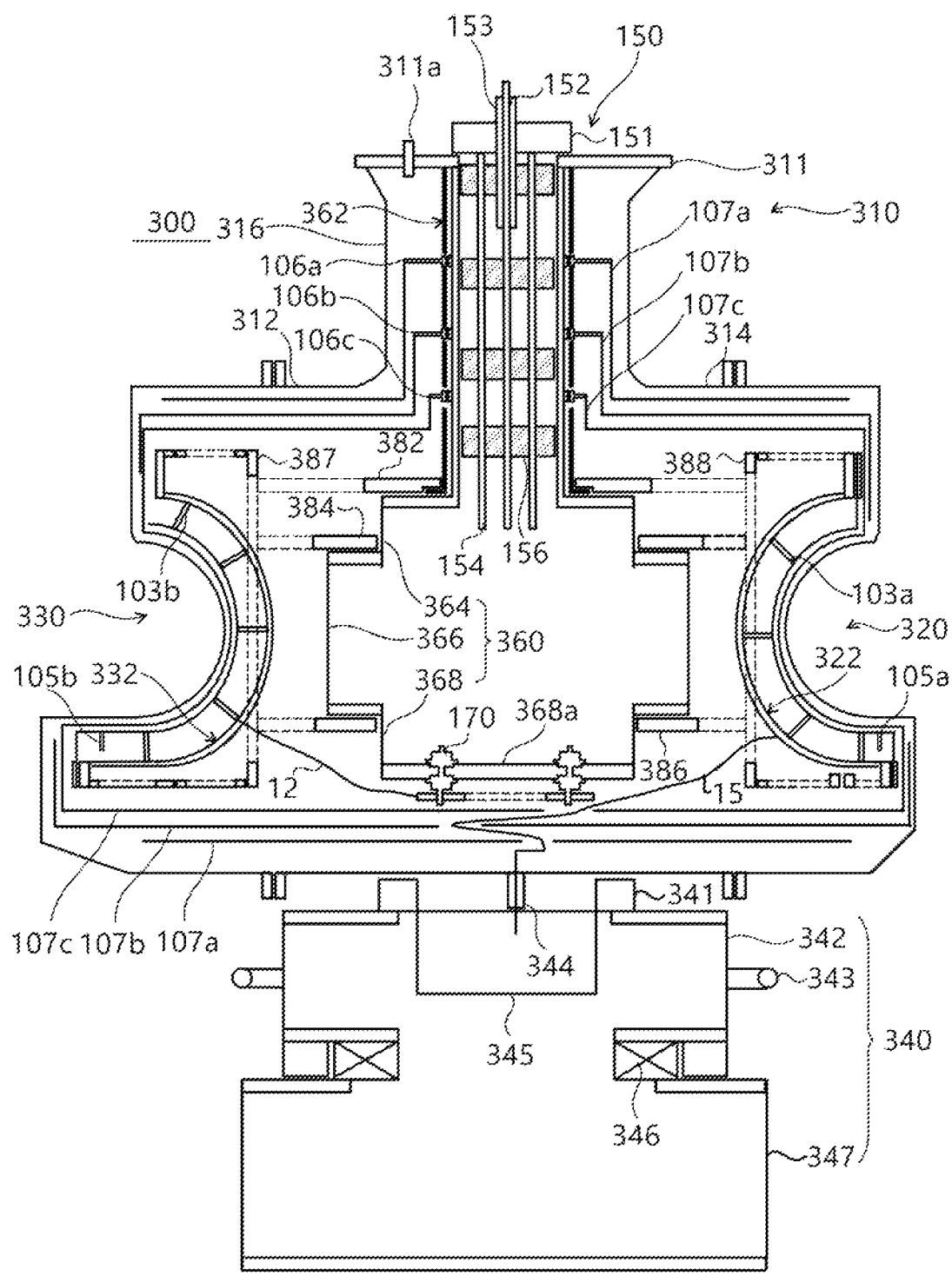
FIG. 3 is a cross-sectional view taken along line A-A' in FIG. 2.

FIG. 3 is a cross-sectional view taken along line A-A' in FIG. 2.

Figure 4:
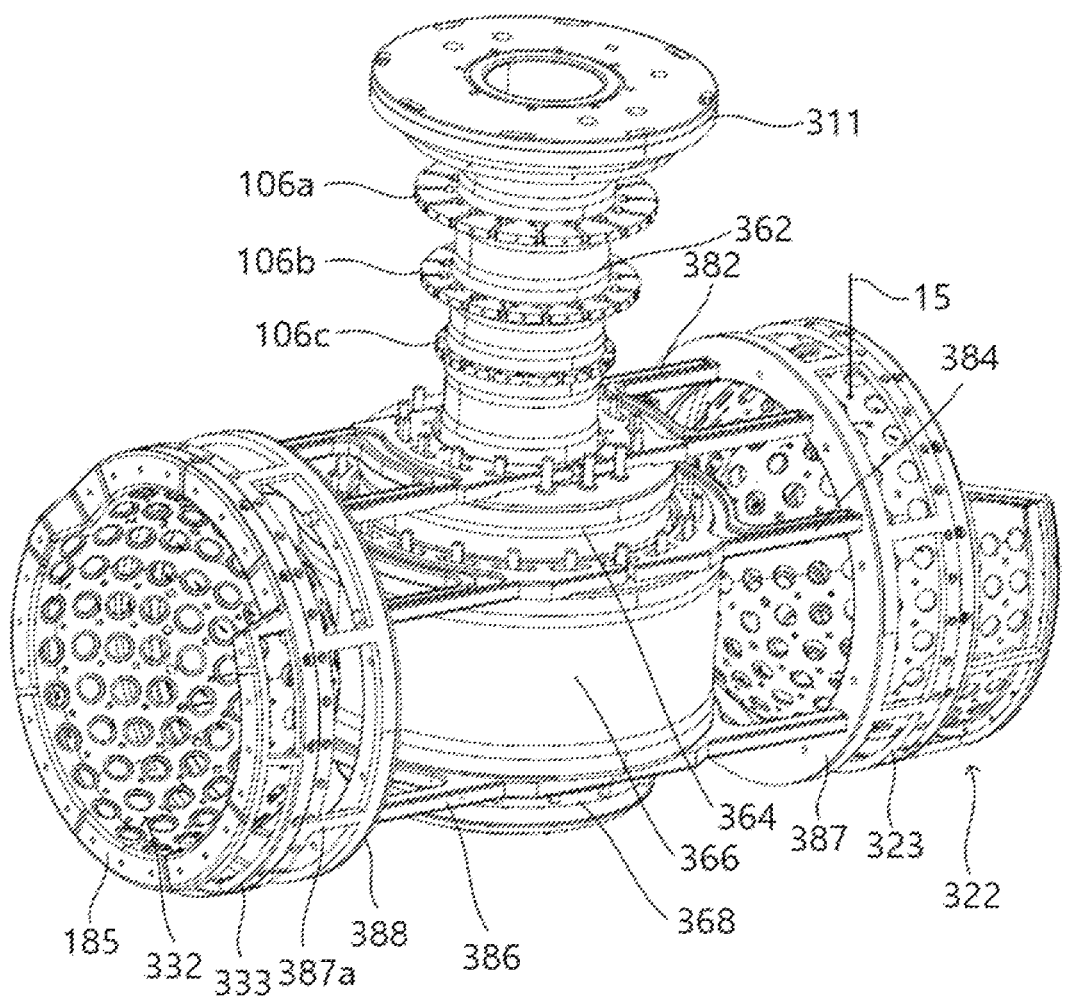
FIG. 4 is a perspective view illustrating an internal container and a sensor-mounted helmet.

FIG. 4 is a perspective view illustrating an internal container and a sensor-mounted helmet.

Figure 5:
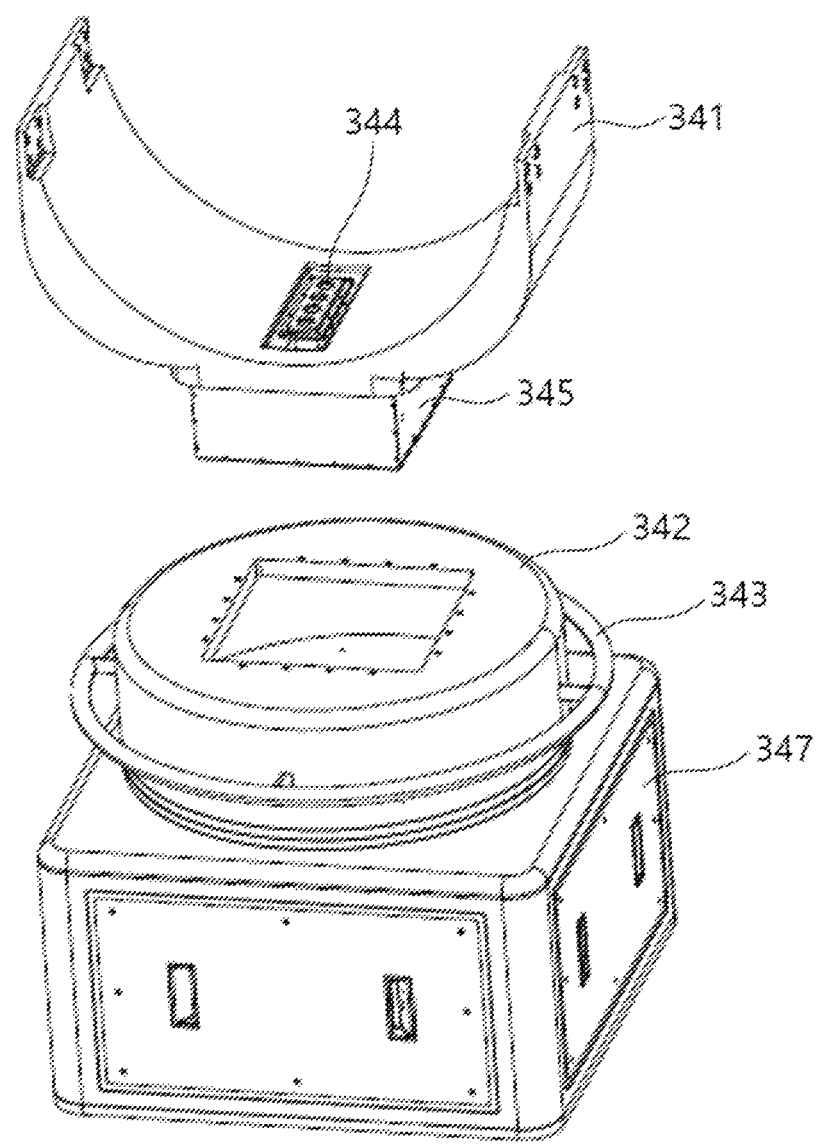
FIG. 5 is an exploded perspective view illustrating a rotational motion unit supporting an external container and providing a rotational motion.

FIG. 5 is an exploded perspective view illustrating a rotational motion unit supporting an external container and providing a rotational motion.

Figure 6:
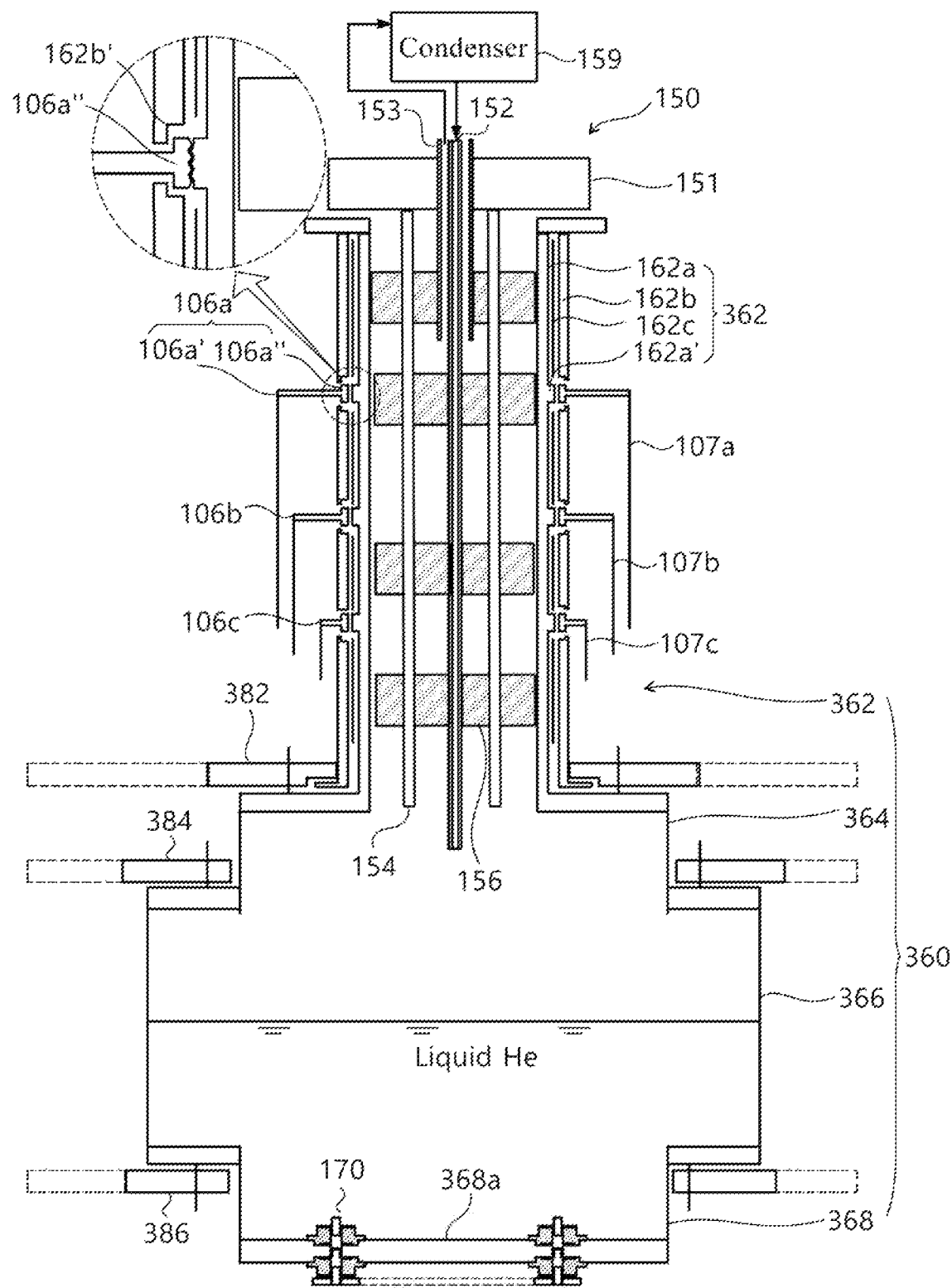
FIG. 6 is an enlarged cross-sectional view of the internal container of the magnetoencephalography measuring apparatus.

FIG. 6 is an enlarged cross-sectional view of the internal container of the magnetoencephalography measuring apparatus.

Referring to FIGS. 1 to 6, a magnetoencephalography measuring apparatus 300 includes an internal container 360 storing a liquid refrigerant, an external container 310 disposed to surround the internal container 360 and including a first external helmet 320 and a second external helmet 330 disposed to be spaced apart from each other, a first sensor-mounted helmet 322 disposed to surround the first external helmet 320 between the external container 310 and the internal container 360, a second sensor-mounted helmet 332 disposed to surround the second external helmet 330 between the externa container 310 and the internal container 360, a plurality of first SQUID sensor module 103*a* disposed on the first sensor-mounted helmet 322, and a plurality of second SQUID sensor module 103*b* disposed on the second sensor-mounted helmet 332. A space between the external container 310 and the internal container 360 is in a vacuum state.

Each of the plurality of first SQUID sensor modules 103*a* is in thermal contact with a main thermal anchor 170 disposed on a lower surface of the internal container 360 through a litz wire 12. Each of the plurality of second SQUID sensor modules 103*b* is in thermal contact with the main thermal anchor 170 disposed on the lower surface of the internal container 360 through the litz wire 12. The space between the external container 310 and the internal container 360 is in a vacuum state. The SQUID sensor of the first helmet-mounted sensor 322 and the second helmet-mounted sensor 332 may be efficiently cooled through the litz wire 12.

The magnetoencephalography measuring apparatus 300 may be disposed inside a magnetically shielded room 11.

The external container 310 may branch off in the form of T. The external container 310 may include a first branch 312 and a second branch 314 branching off from a cylindrical external container body portion 316 in the form of T. Each of the first external helmet 320 and the second external helmet 330 may be coupled to the first branch 312 and the second branch 314, respectively. The first external helmet 320 and the second external helmet 330 may face each other and may have different sizes. A diameter of each of the first branch 312 and the second branch 314 may be greater than a diameter of the external container body portion 316. The first external helmet 320 may include an open portion 321 for securing a view. The external container body portion 316 may be vertically disposed, and the first branch 312 and the second branch 314 may be horizontally disposed. The external container 310 may be a glass fiber reinforced plastic such as G10 epoxy.

The external container body portion 316 may have a cylindrical shape and may rotate about a central axis thereof. The first external helmet 320 or the first external helmet 320 may measure a magnetoencephalography signal for children or adults according to a rotation state of the external container 310.

A rotational motion unit 340 may be coupled to lower surfaces of the first branch 312 and the second branch 314. The rotational motion unit 340 may include a bearing formed of a non-conductive material. The rotational motion unit 340 may be mounted on a bottom of the magnetically shielded room 11.

The first external helmet 320 may be provided with a long groove 320a in a portion coupled to the first branch 312. The first external helmet 320 may rotate along the long groove 320a to be coupled to one end of the first branch 312 in a state of being aligned therewith. The long groove 320a may provide alignment between the first external helmet 320 and the first sensor-mounted helmet 322. The first external helmet 320 may include the open portion 321 for securing a view.

The second external helmet 330 may be provided with a long groove in a portion coupled to the second branch 314. The second external helmet 330 may rotate along the long groove to be coupled to one end of the second branch 314 in a state of being aligned therewith.

The internal container 360 may store a liquid refrigerant, and may cool the SQUID sensor modules 103a and 103b through the main thermal anchor 170 and the litz wire 12. A material of the internal container 360 may be a glass fiber reinforced plastic such as G10 epoxy.

The internal container 360 may include a neck portion 362 into which a baffle insert 150 is inserted, a first body portion 364 having an increased diameter as compared with the neck portion 362, a second body portion 366 having an increased diameter as compared with the first body portion 364; and a third body portion 368 having a decreased diameter as compared with the second body portion. The internal container 360 may include a body portion and a neck portion 362 into which the baffle insert 150 is inserted. The body portion may include a first body portion 364 having an increased diameter as compared with the neck portion 362, a second body portion 366 having an increased diameter as compared with the first body portion, and a third body portion 368 having a decreased diameter as compared with the second body portion.

The neck portion 362 may have a double-wall structure including an internal cylinder and an external cylinder surrounding the internal cylinder. The first body portion 364 may be continuously connected to the neck portion 362. The second body portion 366 may be continuously connected to the first body portion 364. The second body portion 366 may have a greater diameter than the first body portion 364. The third body portion 368 may be continuously connected to the second body portion 366. The third body portion 368 may have a smaller diameter than the second body portion 366. The first body portion 364 and the third body portion 368 may have the same diameter.

The first sensor-mounted helmet 322 and the second sensor-mounted helmet 332 are arranged symmetrically with respect to the first to third body portions 364, 366, and 368 to provide mechanical stability and symmetry of cooling.

A lower surface 368a of the third body portion 368 may include a plurality of getter grooves 368b having a fan shape in a direction toward a lower surface or a vacuum side. A getter, collecting residual gas in a vacuum state, may be disposed in the getter groove 368b.

The neck portion 362 may include an internal cylinder 162a and an external cylinder 162b surrounding the internal cylinder 162a. The heat shielding film 162c may be disposed between the internal cylinder 162a and the external cylinder 162b. The heat shielding layer 162c may have a multilayer structure in which a metal thin film, having high reflectivity and low emissivity, and a significantly thin nonwoven fabric, having low thermal conductivity, are sequentially stacked.

The internal cylinder 162a may further include a plurality of ring projections 162a' protruding outwardly of a cylinder. The ring projection 162a' may have a cylindrical ring shape, and may be formed to be integrated with the internal cylinder 162a. A screw for screw-coupling may be formed on an external circumferential surface of the ring projection 162a'.

The ring projections 162a' may be disposed to be spaced apart from each other. The external cylinder 162b may be separated with the ring projection 162a' interposed therebetween. That is, the external cylinder 162b may include a plurality of cylindrical components separated from each other. A distance between the external cylinder 162b and the internal cylinder 162a may be within several millimeters (mm). Each of the external cylinders 162a may have a raised spot to surround a thermal anchor coupling portion 106a" and the ring projection 162a'. The external cylinder 162b may be coupled to surround the ring projection 162a', a coupling portion may be fixed and sealed with an adhesive such as epoxy.

The thermal anchors 106a, 106b, and 106c may be coupled to the ring projections 162a', respectively. An external circumferential surface of the ring projection 162a' and the internal circumferential surface of the thermal anchors 106a, 106b, 106c may be screw-coupled to each other. Each of the thermal anchors 106a, 106b, and 106c may have a circular washer shape. Each of the thermal anchors 106a, 106b, and 106c may include copper (Cu) or aluminum (Al).

The thermal anchor 106a may include a cylindrical thermal anchor coupling portion 106a" and a disc-shaped thermal anchor body portion 106a' disposed on an external circumferential surface of the coupling portion. An internal circumferential surface of the thermal anchor coupling portion 106a" may be screw-coupled to the external circumferential surface of the ring projection 162a'. Accordingly, the thermal anchors 106a, 106b, and 106c may be stably fixed to the internal container and may be cooled while being in thermal contact with each other through a wide area.

The screw-coupling of the ring projection 162a' and the thermal anchor 106a may improve mechanical stability while providing efficient thermal contact caused by thermal expansion.

The double-wall structure may prevent radiant heat from flowing into the internal container 360 from an external entity. When the internal container is cooled by the refrigerant, a space between the internal cylinder and the external cylinder may be maintained in a vacuum state. Accordingly, heat influx caused by heat transfer may be blocked, and the heat shielding layer 162c may additionally block the influx of the radiant heat. Accordingly, a neck portion of the double-wall structure may provide high mechanical stability and high heat shielding efficiency, as compared with to a neck portion of a single-wall structure.

The thermal anchors 106a, 106b, and 106c may include first to third thermal anchors 106a, 106b, and 106c disposed in order. The first thermal anchor 106a may be disposed on an uppermost side of the neck portion 362, and may be connected to a 120K heat shielding layer 107a. The second thermal anchor 106b may be disposed under the first thermal anchor 106a and connected to an 80K heat shielding layer 107b. The third thermal anchor 106c may be disposed on a lower side of the second thermal anchor 106b, and may be connected to a 40K heat shielding layer 107c. An external diameter of the first thermal anchor 106a may be greater than an external diameter of the second thermal anchor 106b.

The first thermal anchor 106a may be spaced farthest apart from the refrigerant to be maintained at a highest temperature, and the third thermal anchor 106c may be closest to the refrigerant to be maintained at a lowest temperature. The first to third thermal anchors 106a, 106b, and 106c may be in thermal contact with an evaporated refrigerant to be cooled.

The 40K heat shielding layer 107c may be coupled to an external circumferential surface of the third thermal anchor 106c, and may be disposed to surround the internal container 360 to block the influx of radiant heat.

The 40K heat shielding layer 107c may include a heat insulating layer a metal mesh woven with metal wires insulated from each other. The 40K heat shielding layer 107c may branch off in the form of T to surround the first sensor-mounted helmet 322 and the second sensor-mounted helmet 332, and then may surround the first sensor-mounted helmet 322 and the second sensor-mounted helmet 133.

The 80K heat shielding layer 107b may be coupled to an external circumferential surface of the second heat anchor 106b, and may be disposed to surround the 40K heat shielding layer 107c and to block the influx of radiant heat. The 80K heat shielding layer 107b may include a heat insulating layer and a metal mesh woven with metal wires insulated from each other. The 80K heat shield 107b may branch into in the form of T to surround the first sensor-mounted helmet 322 and the second sensor-mounted helmet 332. The 80K heat shield 107b may extend in a direction of a brim of the first sensor-mounted helmet 322, and may extend in a direction of a brim of the second sensor-mounted helmet 332.

The 120K heat shielding layer 107a may be coupled to an external circumferential surface of the first heat anchor 106a, and may be disposed to surround the 80K heat shielding layer 107b and to block the influx of radiant heat. The 120K heat shielding layer 107a may include a heat insulating layer and a metal mesh woven with metal wires insulated from each other. The 120K heat shielding layer 107a may branch off in the form of T to surround the first sensor-mounted helmet 322 and the second sensor-mounted helmet 332.

Each of the heat shielding layers 107a, 107b, and 107c may have an opening in a direction toward the external container support portion 341. The openings may be disposed so as not to overlap each other. Accordingly, signal lines may pass through the openings of the heat shielding layer 107a, 107b, and 107c in a zigzag shape to pass through a vacuum sealing portion 344.

The space between the internal container 360 and the external container 310 may be maintained in a vacuum state. The external container lid 311 may include an exhaust port 311a connected to a vacuum pump. The exhaust port 311a may be formed of a G-10 epoxy tube.

The baffle insert 150 may be disposed to be inserted into the neck portion 362 of the internal container 360. The baffle insert 150 may include an insert upper plate 151, a baffle 156 disposed below the insert upper plate, and a plurality of guide rods 154 supporting the baffle 156 and fixed to the insert upper plate 151.

The insert upper plate 151 may have a disc shape and may be formed of G-10 epoxy. The insert upper plate 151 may be fixed to the external container lid 311. The guide rod 154 is formed of G-10 epoxy, and may have a rod shape or a pipe shape. The guide rod 154 may support the baffle 156. The baffle 156 may include Styrofoam having improved warmth retention and a conductive plate. The conductive plate may include an aluminum-coated Mylar layer and a copper layer sequentially stacked to block the radiant heat.

A refrigerant exhaust tube 153 may be disposed on the insert upper plate of the baffle insert 150, and may exhaust the evaporated refrigerant. The refrigerant injection tube 152 may be disposed on the insert upper plate 151 of the baffle insert 150, and may inject a refrigerant. Each of the refrigerant exhaust tube 153 and the refrigerant injection tube 152 may be a dual tube including an internal tube and an external tube. In the dual tube, a space between the internal tube and the external tube may be maintained in a vacuum state during cooling. The refrigerant injection tube 152 may have a coaxial structure inserted into the refrigerant exhaust tube 153. The refrigerant exhaust tube 153 and the refrigerant injection tube 152 may be formed of G-10 epoxy.

Coaxial dual tubes 152 and 153 may reduce thermal contact with the insert upper plate 151 to reduce ice formation of the insert upper plate 151. When the refrigerant exhaust tube and the refrigerant injection tube are a single tube, the insert upper plate 151 and the refrigerant exhaust tube may form ice to impede sealing of the external container lid 111 and the insert upper plate 151 and to increase influx of external heat. The coaxial dual tubes 152 and 153 may be disposed on a central axis of the insert upper plate 151. One end of the refrigerant exhaust tube 153 may be disposed in a higher location than the first heat anchor 106a. When the external container 310 and the internal container 360 rotate, the coaxial dual tubes 152 and 153 may not rotate while maintaining the sealing using a sealing means such as an O-ring.

The condenser 159 may be connected to the refrigerant exhaust tube 153 and the refrigerant injection tube 152, and may condense the vaporized refrigerant exhausted through the refrigerant injection tube 153. The condenser 159 may be disposed outside the magnetically shielded room 11.

The rotational motion unit 340 may be coupled to lower surfaces of the first branch 312 and the second branch 314. The rotational motion unit 340 may provide a rotational motion of the external container 310.

The rotational motion unit 340 may include an external container support portion 341, an upper support box 342, a lower support box 347, and a bearing portion 346.

The external container support portion 341 may be in the form of C, and may support the lower surfaces of the first branch 312 and the second branch 314. The external container support portion 341 may have a through-hole in a center thereof.

A vacuum sealing portion 344 may be inserted into through-holes formed in the lower surface of the first branch 312 and the second branch 314 to seal signal lines, and be disposed inside the external container support portion 341. The vacuum sealing portion 344 may seal the external container 310 in a vacuum state and the outside in an atmospheric pressure state to each other.

A signal line connection box 345 may be disposed below the external container support portion 341, and may connect the sealed signal lines 15 to each other through the vacuum sealing portion 344. The signal line connection box 345 may be disposed inside the upper support box 342.

The upper support box 342 may be disposed to surround the signal line connection box 345, and may have a cylindrical shape. The upper support box 342 may support the external container support portion 341. A handle 343 may be coupled to an external side of the upper support box 342. A user may rotate the handle 343 to select a rotational state of a magnetoencephalography measuring apparatus.

The lower support box 347 may be disposed below the upper support box 342.

The bearing portion 346 may be disposed between the upper support box 342 and the lower support box 347 to provide a rotational motion of the upper support box 342.

Figure 7:
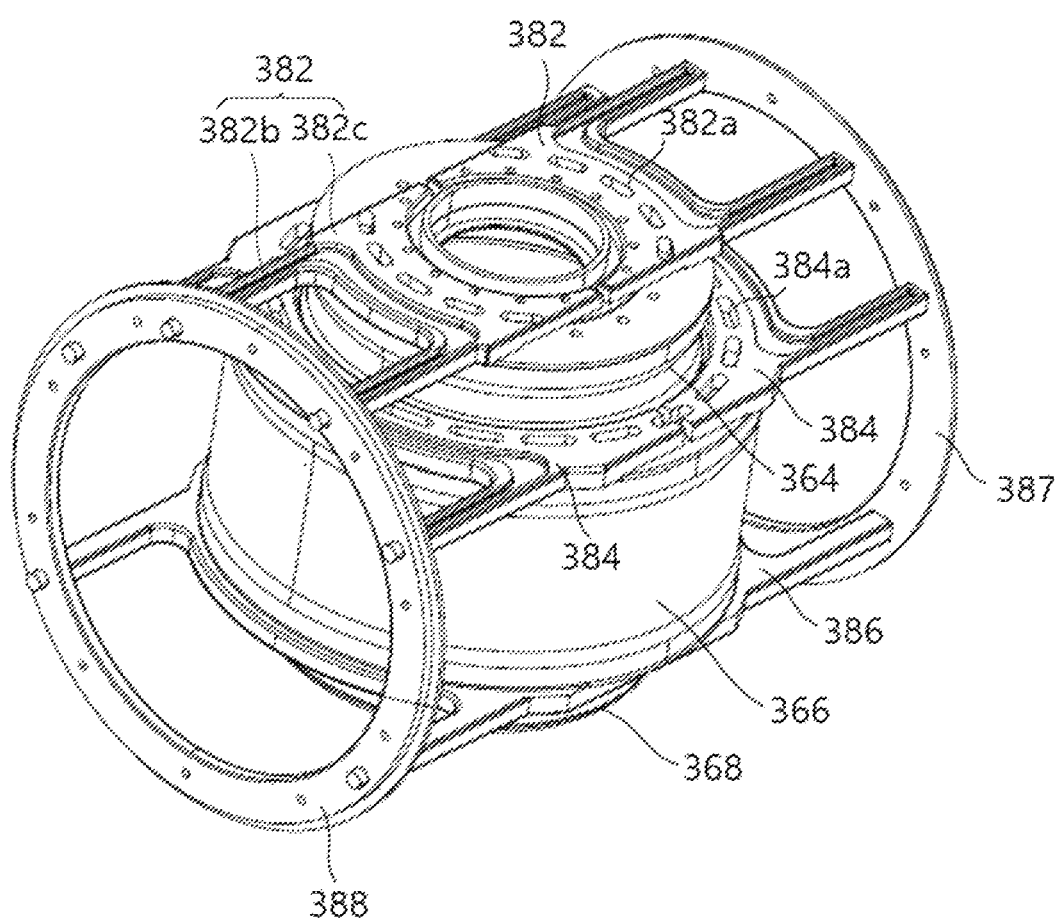
FIG. 7 is a perspective view illustrating a support portion of the sensor-mounted helmet of the magnetoencephalography measuring apparatus.

FIG. 7 is a perspective view illustrating a support portion of the sensor-mounted helmet of the magnetoencephalography measuring apparatus.

Figure 8:
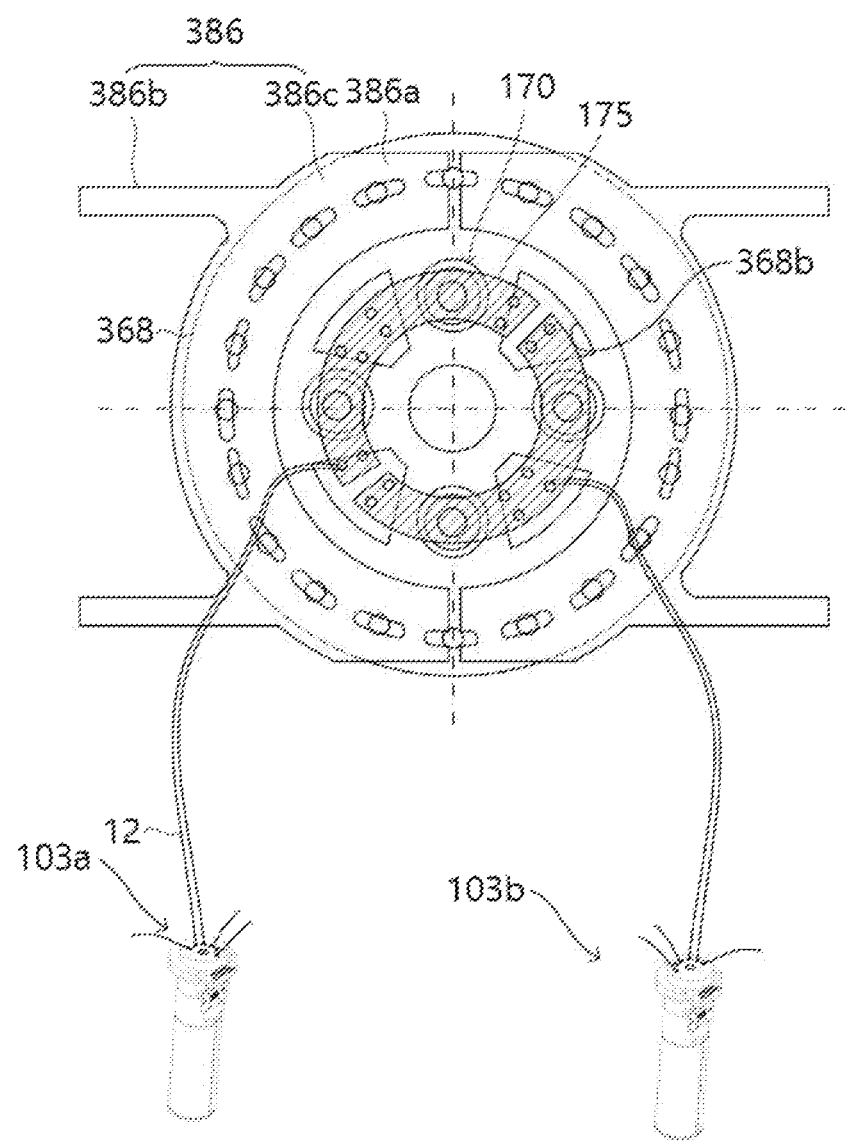
FIG. 8 is a view when viewed from a lower surface of the internal container of the magnetoencephalography measuring apparatus.

FIG. 8 is a view when viewed from a lower surface of the internal container of the magnetoencephalography measuring apparatus.

Figure 9:
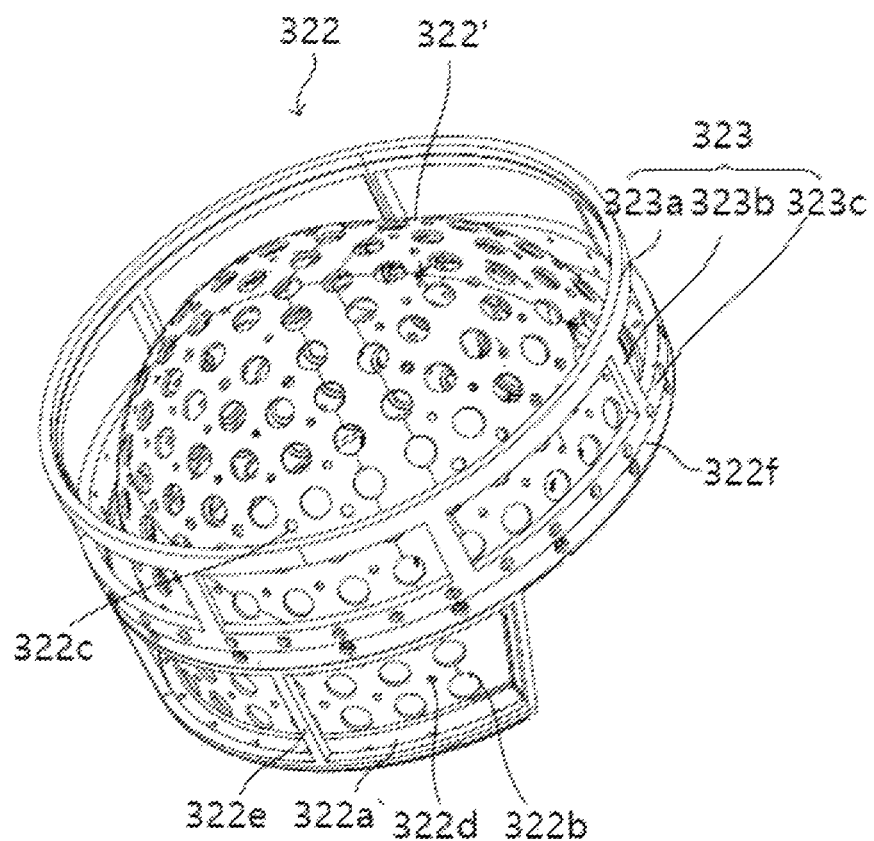
FIG. 9 is a perspective view illustrating a sensor-mounted helmet according to an example embodiment of the present disclosure.
Figure 9:
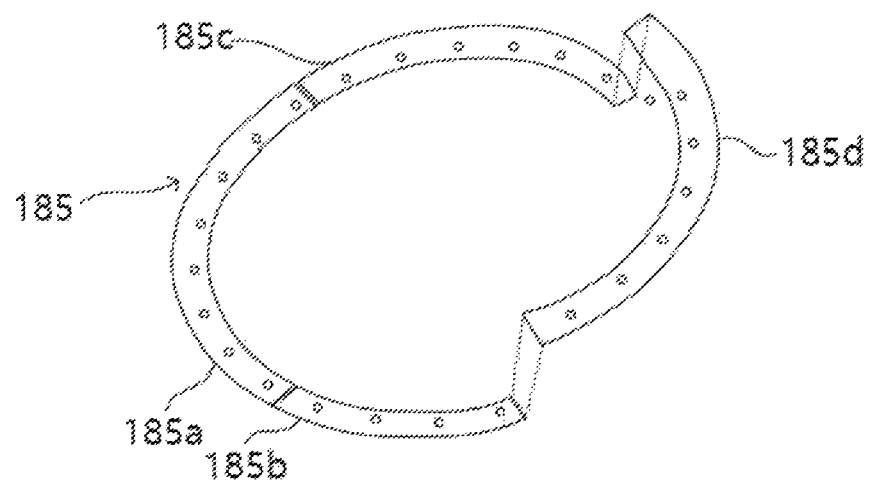

FIG. 9 is a perspective view illustrating a sensor-mounted helmet according to an example embodiment of the present disclosure.

Figure 10:
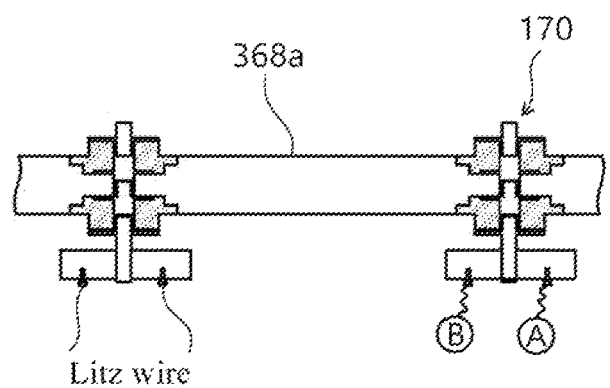
FIG. 10 is a cross-sectional view of the sensor-mounted helmet of FIG. 9.
Figure 10:
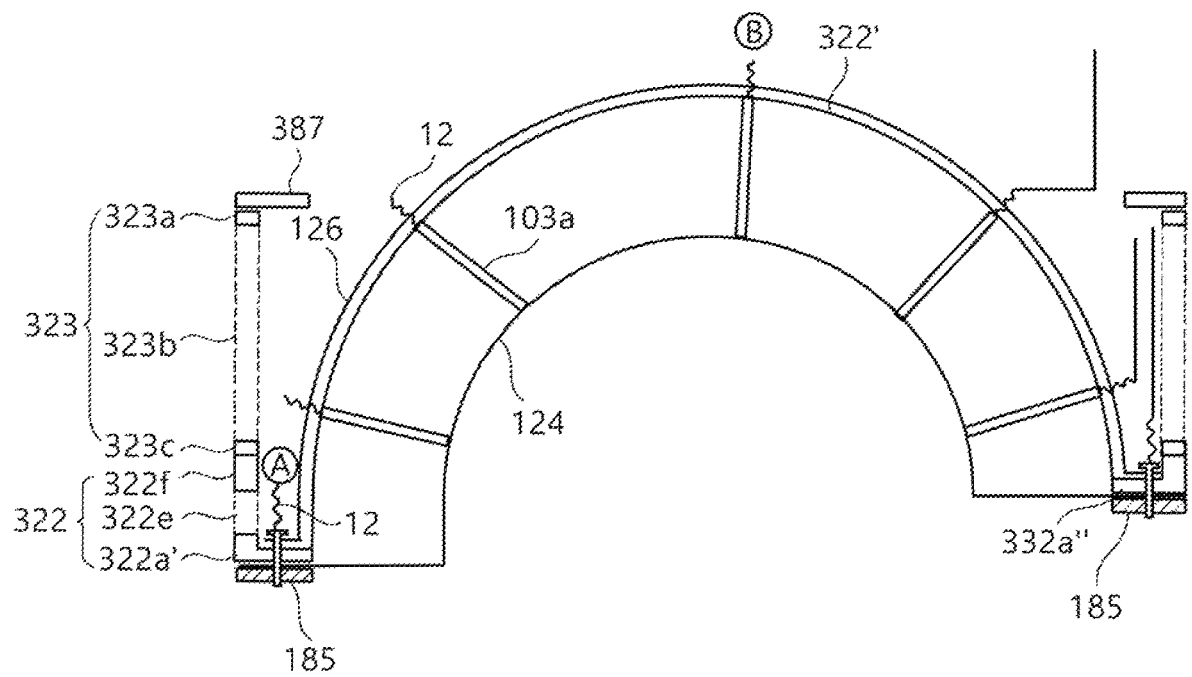

FIG. 10 is a cross-sectional view of the sensor-mounted helmet of FIG. 9.

Referring to FIGS. 7 to 10, a first sensor-mounted helmet 322 may be configured to cover a head, and may include an open portion to secure a subject's view. The first sensor-mounted helmet 322 may include brims 322a' and 322a" on edges thereof. The brim 322a' and 322a" may be connected to a fixing means for fixing the first sensor-mounted helmet 322.

A second sensor-mounted helmet 332 may be configured to cover a head, and includes an open portion to secure a subject's view. The second sensor-mounted helmet 332 may include a brim on an edge thereof. The brim may be connected to a fixing means for fixing the second sensor-mounted helmet 332.

A pair of first support portions 382 may be coupled to an interface between the neck portion 362 and the first body portion 364, and may extend in a direction of the first external helmet 320 and in a direction of the second external helmet 330, respectively. The first support portion 382 may include a C-shaped portion 382c, coupled to the interface between the neck portion 362 and the first body portion 364, and a pair of pillars 382b extending parallel to a direction of a corresponding external helmet. The C-shaped portion 382c may have a plurality of arc-shaped long grooves 382a. A fixing means may be coupled to each of the arc-shaped long grooves 382a to provide alignment with a corresponding sensor-mounted helmet.

A pair of second support portions 384 may be coupled to an interface between the first body portion 364 and the second body portion 366, and extend in the direction of the first external helmet 320 and in the direction of the second external helmet 330, respectively. The second support portion 384 may include a C-shaped portion, coupled to an interface between the first body portion 364 and the second body portion 366, and a pair of pillars extending parallel to a direction of a corresponding external helmet. The C-shaped portion may include a plurality of arc-shaped long grooves 384a. A fixing means may be coupled to each of the arc-shaped long grooves 384a to provide alignment with a corresponding sensor-mounted helmet.

A pair of third support portions 386 may be coupled to an interface between the second body portion 386 and the third body portion 388, and may extend in a direction of the first external helmet 320 and in a direction of the second external helmet 330, respectively. The second support portion 384 may include a C-shaped portion, coupled to an interface between the second body portion 386 and the third body portion 388, and a pair of pillars extending parallel to a direction of a corresponding external helmet. The C-shaped portion may include a plurality of arc-shaped long grooves 386a. A fixing means may be coupled to the arc-shaped long groove to provide alignment with a corresponding sensor-mounted helmet.

A first fixing ring 387 may be coupled to the first support portion 382, the second support portion 384, and the third support portion 386 in a direction of the first external helmet 320.

A second fixing ring 388 may be coupled to the first support portion 382, the second support portion 384, and the third support portion 386 in a direction of the second external helmet 330.

A first auxiliary fixing part 323 may connect the first fixing ring 387 and the first sensor-mounted helmet 322 to each other. The first auxiliary fixing part 323 may include an upper ring 323a, a lower ring 323c spaced apart from the upper ring 323a, and a plurality of support rods 323b connecting the upper ring 323a and the lower ring 323c to each other.

The second auxiliary fixing part 333 may connect the second fixing ring 388 and the second sensor-mounted helmet 332 to each other. The second auxiliary fixing part 333 may include an upper ring, a lower ring spaced apart from the upper ring, and a plurality of support rods connecting the upper ring and the lower ring to each other.

The first sensor-mounted helmet 322 may include brims 322a' and 322a" on edges thereof. The first sensor-mounted helmet 322 may have the same structure as the second sensor-mounted helmet 332, but the first sensor-mounted helmet 322 may be different, in size and the number of SQUID sensor modules, from the second sensor-mounted helmet 332. The first sensor-mounted helmet 322 may have a first through-hole 322b for mounting a SQUID sensor module, a second through-hole 322c for placing a signal line, and a third through-hole for mounting a fixing member for fixing the SQUID sensor module 103a.

The first sensor-mounted helmet 322 may include a helmet body 322' having an open region for securing a view, a lower brim 322a' disposed along an edge of a lower surface of the helmet body, an upper brim 322a" providing a brim in the open portion of the helmet body, a helmet fixing ring 322f having a ring shape at a predetermined interval from the lower brim 322a' and continuously connected to the upper brim 322a", and a plurality of connection pillars 322e vertically connecting the lower brim 322a' and the upper brim 322a" to each other. The brim of the first sensor-mounted helmet 322 may include an upper brim, disposed in an open portion to secure a view, and a lower brim surrounding a subject's occipital region.

The first auxiliary thermal anchor 185 may be disposed on a lower surface of the brim 322a of the first sensor-mounted helmet 322. The first auxiliary thermal anchor 185 may be divided into a plurality of components 185a to 185d. The first auxiliary thermal anchor 185 may be fabricated using an oxygen-free copper strip. The divided first auxiliary thermal anchor 185 may be divided into four pieces to reduce eddy current noise, caused by high-frequency magnetic noise, and thermal noise, caused by free electrons of a metal, and may provide a uniform location-dependent temperature gradient. The first auxiliary thermal anchor 185 may be in thermal contact with the main thermal anchor 170 by a litz wire 12.

A first internal 4K heat shielding portion 124 may be in thermal contact with the first auxiliary thermal anchor 185, and may be disposed on an internal side surface of the first sensor-mounted helmet 322. The first internal 4K heat shielding portion 124 may be disposed to surround the SQUID sensor modules 103a, and may include an insulation-coated metal mesh.

A first external 4K heat shielding portion 126 may be in thermal contact with the first auxiliary thermal anchor 185, and may be disposed on an external side surface of the first sensor-mounted helmet 322. The first external 4K heat shielding portion 126 may be disposed to surround an external side surface of the first sensor-mounted helmet 322. The first external 4K heat shielding portion 126 may include an insulation-coated metal mesh. Accordingly, the first auxiliary heat anchor 185, the first internal 4K heat shielding portion 124, and the first external 4K heat shielding portion 126 may be in thermal contact with the main heat anchor 170 by a litz wire 12.

A second auxiliary thermal anchor may be disposed on a lower surface of the brim of the second sensor-mounted helmet 332. A second internal 4K heat shielding portion may be in thermal contact with the second auxiliary thermal anchor, and may be disposed on an internal side surface of the second sensor-mounted helmet 332. The second external 4K heat shielding portion may be in thermal contact with the second auxiliary thermal anchor, and may be disposed on an external side surface of the second sensor-mounted helmet. The second auxiliary heat anchor, the second internal 4K heat shielding portion, and the second external 4K heat shielding portion may be in thermal contact with the main heat anchor 170 through a litz wire 12.

Figure 11:
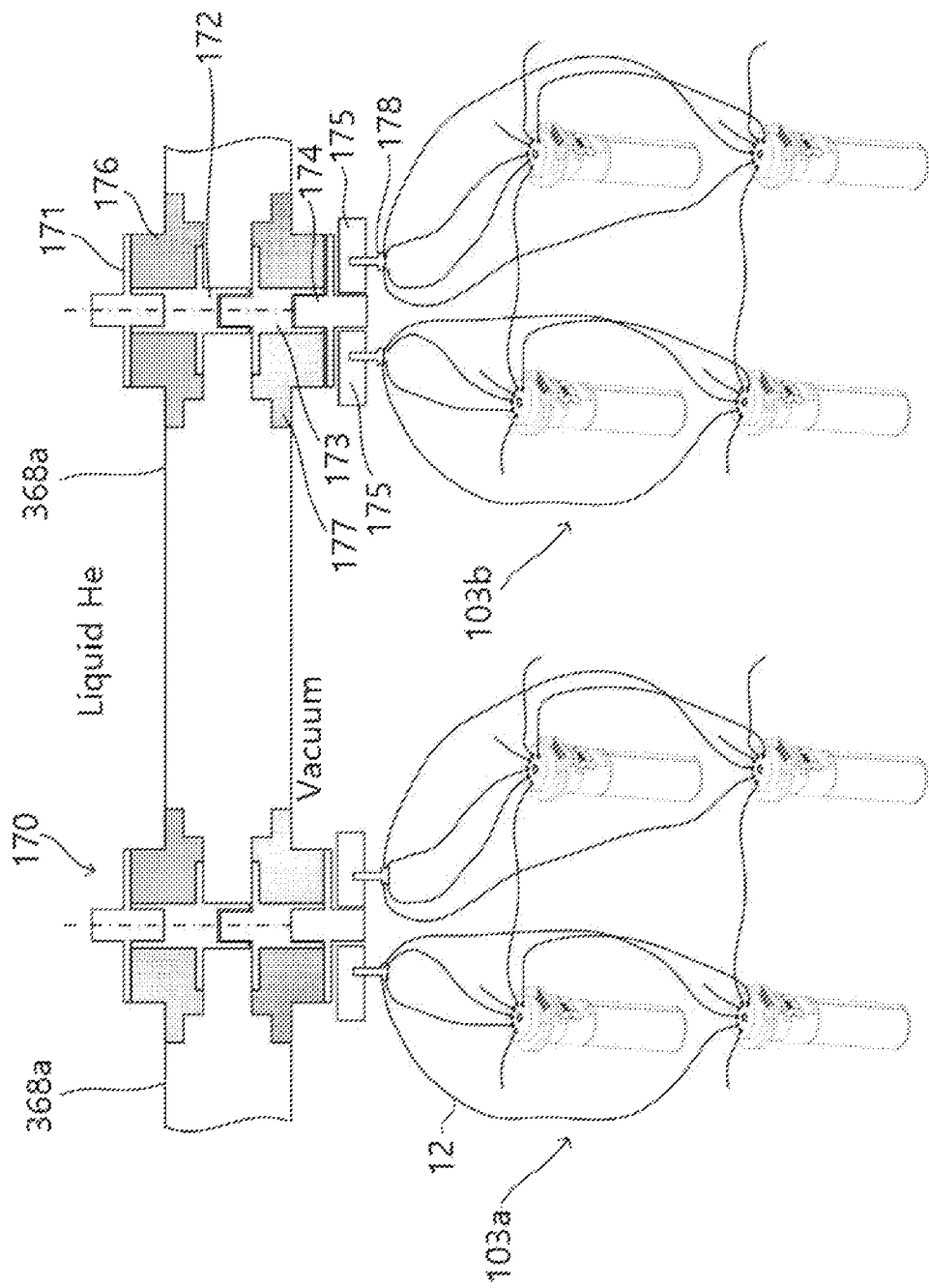
FIG. 11 is a conceptual diagram illustrating a connection relationship between a main thermal anchor and a SQUID sensor module according to an example embodiment of the present disclosure.

FIG. 11 is a conceptual diagram illustrating a connection relationship between a main thermal anchor and a SQUID sensor module according to an example embodiment of the present disclosure.

Figure 12:
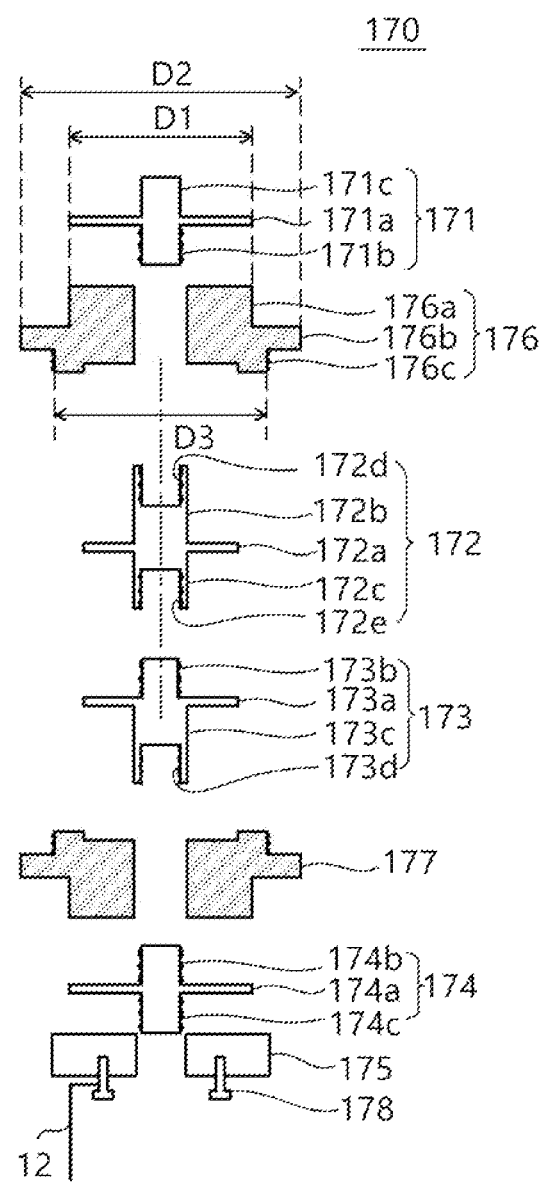
FIG. 12 is a cross-sectional view of the main thermal anchor.

FIG. 12 is a cross-sectional view of the main thermal anchor.

Referring to FIGS. 11 and 12, each of the plurality of first SQUID sensor modules 103a may be in thermal contact with a main thermal anchor 170 disposed on the lower surface of the internal container 360 through a litz wire 12. Each of the plurality of second SQUID sensor modules 103b may be in thermal contact with the main thermal anchor 170 disposed on the lower surface of the internal container 360 through the litz wire 12.

The main heat anchor 170 may include a first heat transfer unit 171, a second heat transfer unit 172, a third heat transfer unit 173, a fourth heat transfer unit 174, a fifth heat transfer unit 175, a first thermal expansion control unit 176, and a second thermal expansion control unit 177. The main thermal anchor 170 may include of a plurality of components to increases a thermal contact area while inhibiting damage to the internal container caused by thermal expansion, and thus, may efficiently cool a litz wire 12 and a SQUID sensor.

The first thermal expansion control unit 176 may be coupled to a double groove having two radii formed on an internal side of the lower surface of the internal container, and the second thermal expansion control unit 177 may be coupled to a double groove having two radii formed on an external side of the lower surface of the internal container.

The first heat transfer unit 171 may be formed of oxygen-free copper, and may include a first disc 171a and a first lower projection 171b protruding from a central axis of the first disc 171a to a lower surface of the first disc 171a. The first heat transfer unit 171 may further include a first upper projection 171c protruding from the central axis of the first disc 171a to an upper surface of the first disc 171a.

The second heat transfer unit 172 may be formed of oxygen-free copper, and may include a second disc 172a, a second upper projection 172b protruding from a central axis of the second disc 172a to an upper surface of the second disc 172a, and a second lower projection 172c protruding from the central axis of the second disc 172a to a lower surface of the second disc 172a. The second upper projection 172b of the second heat transfer unit 172 may include a screw groove 172d for coupling to the first lower projection 171b of the first heat transfer unit 171. The second lower projection 172c of the second heat transfer unit 172 may have a screw groove 172e for coupling to the third upper projection 173b of the third heat transfer unit 173.

The third heat transfer unit 173 may be formed of oxygen-free copper, and may include a third disc 173a, a third upper projection 173b protruding from a central axis of the third disc 173a to an upper surface of the third disc 173a, and a third lower projection 173c protruding from the central axis of the third disc 173a to a lower surface of the third disc 173a. The third lower projection 173c of the third heat transfer unit 173 may have a screw groove 173d for coupling to the fourth upper projection 174b of the fourth heat transfer unit 174.

The fourth heat transfer unit 174 may be formed of oxygen-free copper, and may include a fourth disc, a fourth upper projection 174b protruding from a central axis of the fourth disc to an upper surface of the fourth disc, and a fourth lower projection 174c protruding from the central axis of the fourth disc to a lower surface of the fourth disc.

The fifth heat transfer unit 175 may be formed of oxygen-free copper, and may include a C-shaped plate. The fifth heat transfer unit 175 may be coupled to the fourth lower projection 174c of the fourth heat transfer portion 174. A lower surface of the fifth heat transfer unit 175 may be coupled to a fixing means 178. The fixing means 178 may fix and cool the litz wire 12 connected to the SQUID sensor module 103a.

The first thermal expansion control unit 176 may be formed of an insulating material, or and may be inserted between the first disc 171a of the first heat transfer unit 171 and the second disc 172b of the second heat transfer unit 172. The first thermal expansion control unit 176 may include the same material as the internal container.

The second thermal expansion control unit 177 may be formed of an insulating material, and may be inserted between the third disc 173a of the third heat transfer unit 173 and the fourth disc 174a of the fourth heat transfer unit 174. The second thermal expansion control unit 177 may include the same material as the internal container.

The first thermal expansion control unit 176 may include a first insulating body portion 176a having the same diameter as a first diameter D1 of the first disc 171a, a second insulating body portion 176b embedded in a lower surface of the internal body and having a second diameter D2 greater than the first diameter D1, and a third insulating body portion 176c having a third diameter D3 smaller than the second diameter D2. The third insulating body portion 176c may be disposed to surround an external circumferential surface of the second disc 172a. An external circumferential surface of the third insulating body portion 176c may be provided with a screw groove.

The second thermal expansion control unit 177 may have the same structure as the first thermal expansion control unit 176.

When the first to fourth heat transfer units 171 to 174 are coupled to each other, the first thermal expansion control unit 176 and the second thermal expansion control unit 177 may be pressed to be sealed with the internal container. In addition, the first disc 171a and the fourth disc 174a may be sealed by pressing the first thermal expansion control unit 176 and the second thermal expansion control unit 177.

The main thermal anchor 170 may cool the first SQUID sensor module 103a and the second SQUID sensor module 103b through a litz wire.

Each of the first SQUID sensor modules 103a may be cooled by a plurality of litz wires 12. Some of the plurality of Litz wires 12 may be provided to a neighboring first SQUID sensor module 103a. The remainder of the plurality of litz wires 12 may be in thermal contact with the main thermal anchor 170.

Each of the first SQUID sensor modules 130a may be cooled by six litz wires 12. Two litz wires 12 may be in thermal contact with the main thermal anchor 170, and the rest four litz wires 12 may be connected to a neighboring first SQUID sensor module 103a.

Each of the first SQUID sensor modules 103a may be inserted into a through-hole, formed in the first sensor mounting helmet 322, to be fixed.

The first SQUID sensor module 103a may have a plurality of holes 611. The litz wire 12 may be inserted into the holes 611 to cool the SQUID sensor 646.

Figure 13A:
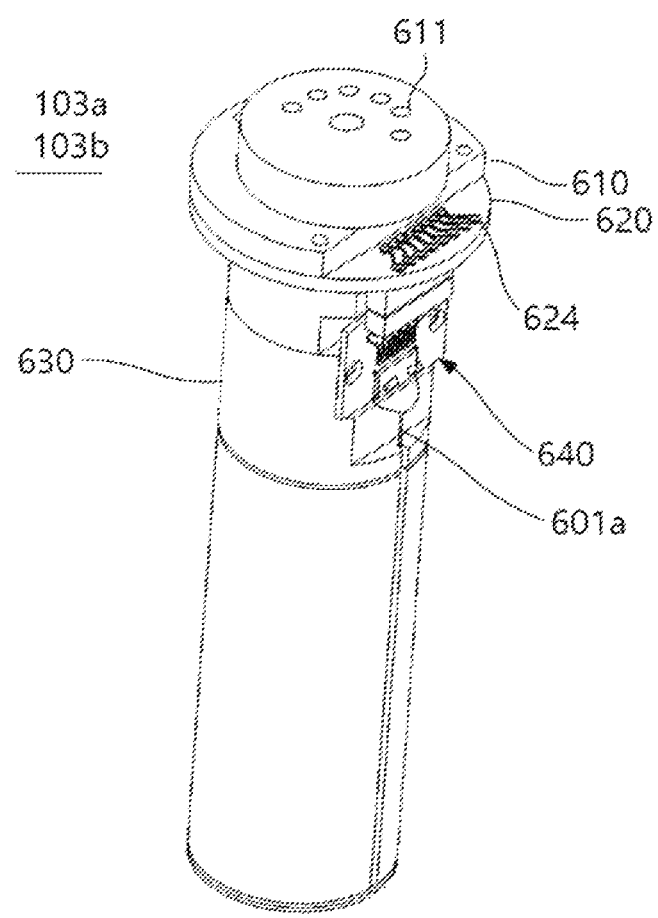
FIG. 13A is a perspective view illustrating a SQUID sensor module according to an example embodiment of the present disclosure.

FIG. 13A is a perspective view illustrating a SQUID sensor module according to an example embodiment of the present disclosure.

Figure 13B:
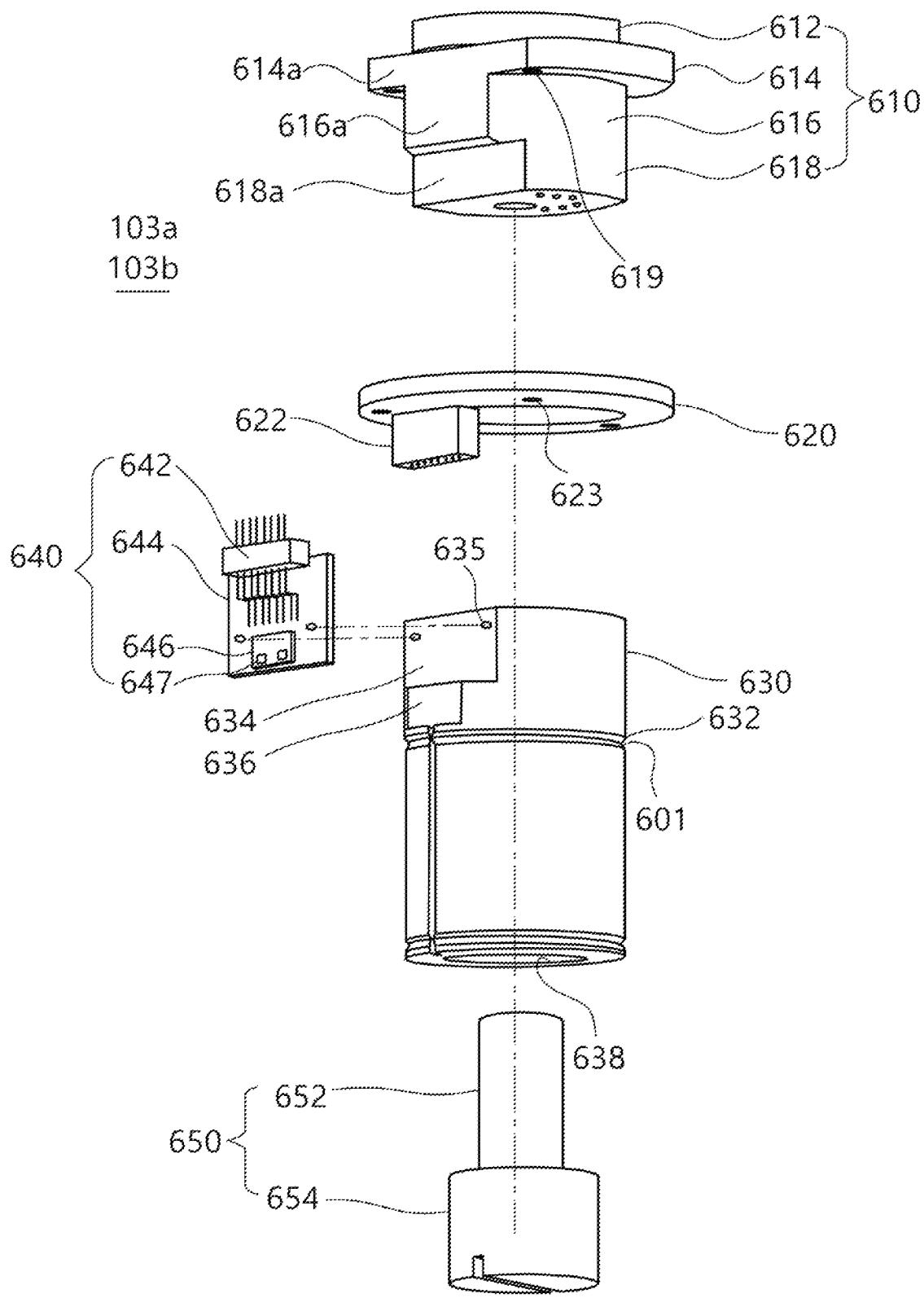
FIG. 13B is an exploded perspective view illustrating the SQUID sensor module of FIG. 13A.

FIG. 13B is an exploded perspective view illustrating the SQUID sensor module of FIG. 13A.

Figure 13C:
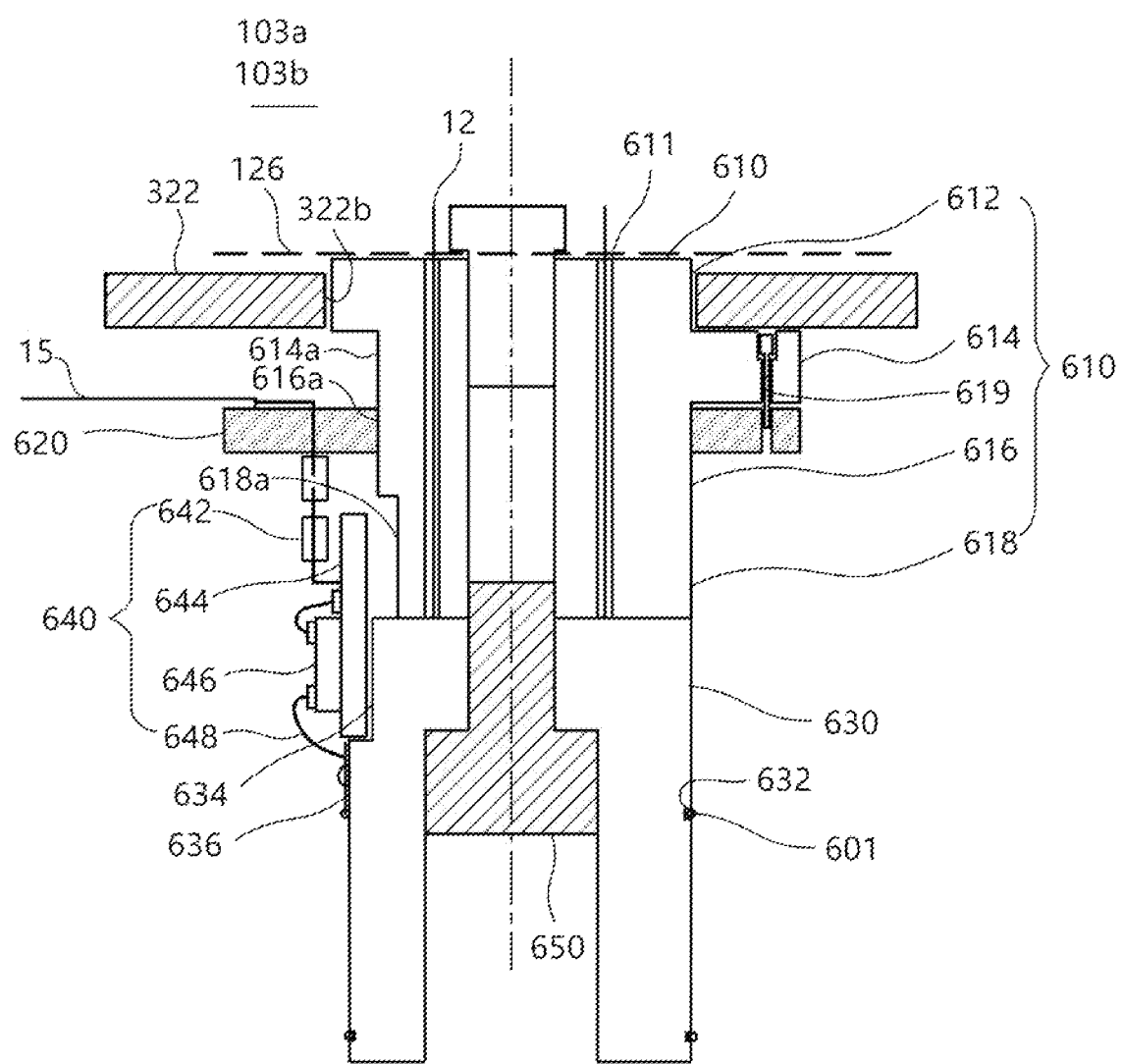
FIG. 13C is a cross-sectional view illustrating a SQUID sensor module according to an example embodiment of the present disclosure.

FIG. 13C is a cross-sectional view illustrating a SQUID sensor module according to an example embodiment of the present disclosure.

Referring to FIGS. 13A to 13C, a SQUID sensor module 103a/103b may include a fixed block 610 having one end fixed to a sensor-mounted helmet 122/132, a bobbin 630 having one end coupled to the other end of the fixed block 610 and provided with a groove around which a pick-up coil 601 is wound, a bobbin fixing means 650 fixed to the other end of the fixed block 610 through a through-hole formed in a center of the bobbin 630, a superconducting quantum interference device (SQUID) printed circuit board (PCB) 640 disposed on an upper side surface of the bobbin 630 and including a SQUID sensor 646, and a signal line connection PCB 620 inserted into an external circumferential surface of the fixed block 610 and transferring a signal, detected by the SQUID sensor 646, to an external circuit.

The sensor-mounted helmets 122 and 132 may mount a SQUID sensor module 600, and may be disposed in a vacuum space between an external container and an internal container. The sensor-mounted helmets 122 and 132 may be formed of a non-magnetic material. The sensor-mounted helmets 122 and 132 may include a first sensor-mounted helmet 322 and a second sensor-mounted helmet 332 mounting a SQUID sensor module.

The fixed block 610 may be formed of a non-magnetic material, such as G10 epoxy, in an integral type. The fixed block 610 may be inserted into the through-hole 122b formed in the sensor-mounted helmet to be fixed through an adhesive. The fixed block 610 may include a fixed block projection 612, a fixed block threshold portion 614, a fixed block body portion 616, and a fixed block extending portion 618. The fixed block 610 may have a plurality of holes 611 in a central axis direction in which a litz wire for cooling is inserted. The litz wire may be inserted into each of a plurality of holes 611 to cool the SQUID sensor 646.

The fixed block projection 612 may have a disc shape, and may be coupled to a groove or a through-hole 122b formed in the sensor-mounted helmet. In addition, the fixed block projection 612 may be fixed to the through-hole through an adhesive.

The fixed block threshold portion 614 may have a disc shape and may be continuously connected to the fixed block projection portion 612. The fixed block threshold portion 614 may have a greater diameter than the fixed block projection 612. The fixed block threshold portion 614 may have a planar side surface 614a. One side surface 614a of the fixed block threshold 614 may be a plane having a predetermined first vertical distance from a central axis having a cylindrical shape. The fixed block threshold portion 614 may serve to perform an alignment in a central axis direction. A through-hole 619 may be formed in an exterior of the fixed block threshold 614.

The fixed block body portion 616 may be a portion coupled to the signal line connection PCB 620. The signal line connection PCB 620 may be disposed to be inserted into the external peripheral surface of the fixed block body portion 616. The signal line connection PCB 620 may include a hole 623 on an external periphery thereof. The through-hole 619 of the fixed block threshold 614 may be aligned with the hole 623 of the signal line connection PCB 620. The fixing means may be inserted into the through-hole 619 of the fixed block threshold portion 614 and the hole 623 of the signal line connection PCB 620 to fix the fixed block threshold portion 614 and the signal line connection PCB 620 to each other. An internal diameter of the signal line connection PCB 620 may be substantially the same as an external diameter of the fixed block body portion 616. In addition, the external diameter of the signal line connection PCB 620 may be substantially the same as an external diameter of the fixed block threshold 614.

The signal line connection PCB 620 has a washer shape having a central through-hole therein. When the signal line connection PCB 620 is coupled to the external circumferential surface of the fixed block 610, one side of the central through-hole may be planar so as to inhibit a rotational motion. The signal line connection PCB 620 may include a first connector 622. The first connector 622 may be a female connector. The first connector 622 may be disposed on an edge of a lower surface of the signal line connection PCB 620. A connection terminal 624 and a wiring may be disposed on an upper surface of the signal line connection PCB 620. The connection terminal 624 may be connected to the first connector 622 through the wiring. A connection wire, connected to an external circuit, may be coupled to the connection terminal 624.

The fixed block body portion 616 may have a disc shape and may be continuously connected to the fixed block threshold portion 614. The fixed block body portion 616 may have a smaller diameter than the fixed block threshold portion 614, and may have a planar side surface 616a. One side surface 616a of the fixed block body portion 616 may be a plane having a predetermined second vertical distance from the central axis having a cylindrical shape.

The fixed block extending portion 618 may have the same diameter as the fixed block body portion 616, and may have a planar side surface 618a. The side surface 618a may be a plane having a predetermined third vertical distance from the central axis having a cylindrical shape. The third vertical distance may be smaller than the second vertical distance.

One planar side surface 614a of the fixed block threshold portion 614 and one planar side surface 616a of the fixed block body portion 616 may be connected to each other. The one side surface 616a of the fixed block body 616 and the one side surface 618a of the fixed block extending portion 618 may be spaced apart from each other to be parallel to each other. A vertical distance between a central axis and one side surface of the fixed block extending portion 618 may be smaller than a vertical distance between the central axis and one side surface of the fixed block body portion 616.

The bobbin 630 may be formed of a non-magnetic material such as G10 epoxy. The bobbin 630 may have a cylindrical shape. The bobbin 630 includes a first planar portion 634, formed on an upper side surface having a first vertical distance from the central axis, and a second planar portion 634 formed on a lower side surface 636 having a second vertical distance larger than the first vertical distance. The bobbin 630 may have a groove 632 formed around a lower side surface thereof. The groove may form a closed loop. A pick-up coil 601 may be wound around the groove 632. A hole 635 may be formed in the first planar portion 634. The hole 635 may be coupled to a fixing means for fixing the SQUID PCB 640. The SQUID PCB 640 may be disposed on the first planar portion 634. Both ends of the pick-up coil 601 may be fixed to the second planar portion 636 through an adhesive. The pick-up coil 601 may be electrically connected to the SQUID sensor 646 through a connection line 648 formed of a superconductor material. The connection line 648 may include a niobium (Nb) material.

The SQUID PCB 640 may include a second connector 642 and a SQUID sensor 646 and disposed on a PCB substrate 644. The SQUID sensor 646 may be in the form of a semiconductor chip. The SQUID sensor 646 may include an input coil and a Josephson junction. The SQUID sensor 646 may include a conductive pad for electrical connection to the pick-up coil 601. The conductive pad may connect the pick-up coil 601. The second connector 642 may be electrically connected to another conductive pad. The second connector 642 may be a pin-type male connector. Accordingly, the second connector 642 may be separated from or coupled to the first connector 622.

The pick-up coil 601 may be a first-order axial gradiometer. Therefore, a length of a bobbin, around which the pick-up coil 601a is wound, may be increased. The pick-up coil 601 may include a pair of one-turn coils continuously connected and wound in directions opposite to each other. The pick-up coil 601 and the SQUID sensor 646 are bonded to be directly connected to each other using a connection line 648 of a thermally treated superconducting material, and an integral-type QUID magnetometer may be manufactured. A material of the pick-up coil 601 may be a niobium-tantalum (NbTi) wire.

The connection line of a niobium (Nb) material, used for bonding, may be subject to a vacuum heat treatment at a temperature 1900 degrees Celsius to increase ductility. Superconducting bonding may be performed using an ultrasonic wedge bonder. Both end portions of the pick-up coil may be twisted together. Accordingly, noise of the pick-up coil may be significantly reduced. The pick-up coil may be a first-order gradiometer or a magnetometer.

The bobbin fixing means 650 may be inserted into a through-hole 638 penetrating through a central axis of the bobbin 630. Thus, the bobbin fixing means 650 may be fixed to a lower surface of the fixed block 610. The bobbin fixing means 650 may include a non-magnetic material such as G10 epoxy.

When the SQUID PCB 640 malfunctions, the bobbin fixing means 650 may be removed to replace the SQUID PCB 640. In this case, the bobbin 630 and the fixed block 610 may be separated from each other. Thus, the malfunctioning SQUID PCB may be simply replaced with a new SQUID PCB. As a result, maintenance may be facilitated.

The SQUID sensor module 103a/103b may include a fixed block 610 having one end fixed to a support portion, a bobbin 630 having one end coupled to the other end of the fixed block 610 and having a groove around which a pick-up coil 601a is wound, a bobbin fixing means fixed to the other end of the fixed block 610 through a through-hole formed in a center of the bobbin 630, a superconducting quantum interference device (SQUID) printed circuit board (PCB) 640 including a SQUID sensor, and a signal line connection PCB 620 inserted into an external circumferential surface of the fixed block 610 and transferring a signal, detected by the SQUID sensor, to an external circuit.

Figure 14:
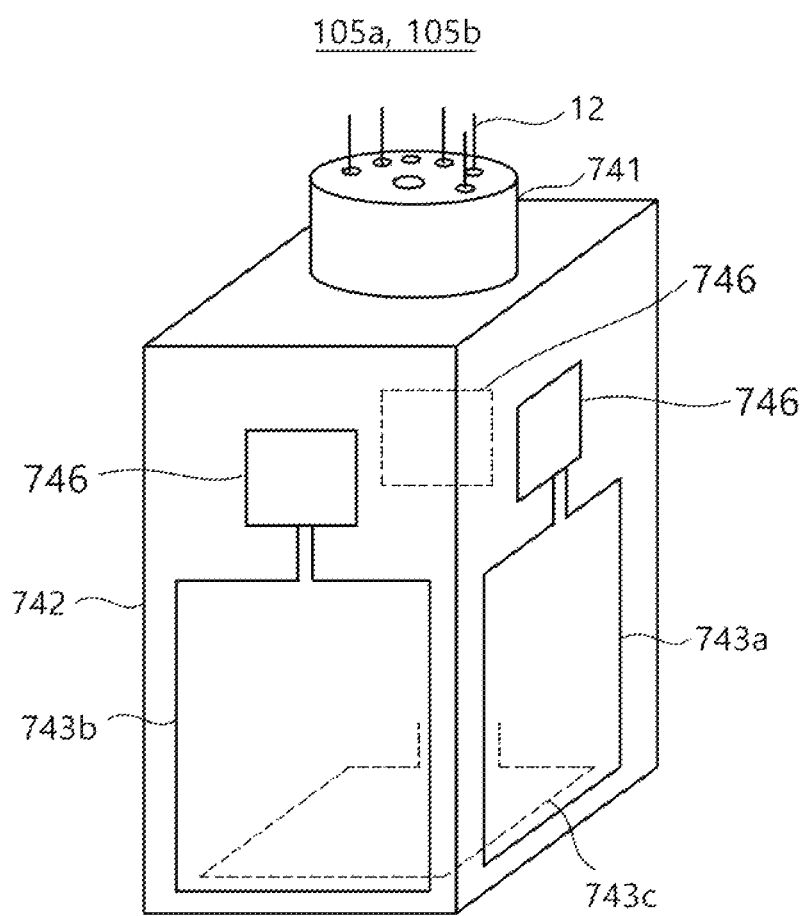
FIG. 14 is a perspective view illustrating a SQUID sensor module according to another example embodiment of the present disclosure.

FIG. 14 is a perspective view illustrating a SQUID sensor module according to another example embodiment of the present disclosure.

Referring to FIGS. 3 and 14, a first reference SQUID sensor module 105a may be disposed on a first sensor-mounted helmet 322, and a second reference SQUID sensor module 105b may be disposed on a second sensor-mounted helmet 332. The first reference SQUID sensor module 105a may be used as a sensor measuring a background magnetic field while the second SQUID sensor module 103b is operating. The second reference SQUID sensor module 105b may be used as a sensor measuring a background magnetic field while the first SQUID sensor module 103a is operating.

Each of the first reference SQUID sensor module 105a and the second reference SQUID sensor module 105b may be a triaxial magnetic field sensor. Each of the first reference SQUID sensor module 105a and the second reference SQUID sensor module 105b may include a first pick-up coil 743a detecting a magnetic field component in an x-axis direction, a second pick-up coil 743b detecting a magnetic field component in a y-axis direction, and a third pick-up coil 743c detecting a magnetic field component in a z-axis direction. Each of the first to third pick-up coils 743a to 743c may be connected to the SQUID sensor 746.

The first reference SQUID sensor module 105a may include a cylindrical fixed block 741 and a bobbin 742 in which a pick-up coil, coupled to the fixed block 741, is disposed. The bobbin 742 may have a rectangular parallelepiped shape. The fixed block 741 may have through-holes in a plurality of central-axis directions, and litz wires 12 may be inserted into the through-holes. The litz wires 12 may be connected to a main thermal anchor 170.

As described above, a magnetoencephalography (MEG) measuring apparatus according to an example embodiment may measure magnetoencephalography of children's MEG or adults' MEG according to a rotation state using a helmet for children and a helmet for adults, respectively disposed on both ends of a barrel-shaped Dewar placed horizontally in a narrow magnetically shielded room.

A magnetoencephalography (MEG) measuring apparatus according to an example embodiment may efficiently block radiant heat using a neck portion having a double-wall structure in a barrel-shaped Dewar placed horizontally.

A magnetoencephalography (MEG) measuring apparatus according to an example embodiment may measure children's MEG or adults' MEG according to a rotation state by placing a rotational motion unit, providing a rotational motion, on the ground in a barrel-shaped Dewar disposed horizontally.

A magnetoencephalography (MEG) measuring apparatus according to an example embodiment may increase efficiency of a condenser or a cooler by transferring a low-temperature refrigerant to the condenser while providing a rotation motion using a coaxial dual-tube structure connecting the condenser and a Dewar to each other.

A magnetoencephalography (MEG) measuring apparatus according to an example embodiment may employ a coil-in-vacuum structure, and thus, may decrease a distance between a SQUID sensor and a current source to increase a signal-to-noise ratio (SNR).

A magnetoencephalography measuring apparatus according to an example embodiment of the present disclosure may include a main thermal anchor for cooling a SQUID sensor on a lower surface of an internal container storing a refrigerant. The main thermal anchor may include a plurality of components to increase a thermal contact area while inhibiting damage to the internal container caused by thermal expansion. Thus, a litz wire and the SQUID sensor may be efficiently cooled.

Although the present disclosure and its advantages have been described in detail, it should be understood that various changes, substitutions and alterations can be made herein without departing from the spirit and scope of the disclosure as defined by the following claims.

What is claimed is:

1. A dual-helmet magnetoencephalography measuring apparatus comprising:
    an internal container comprising a glass fiber-reinforced plastic and storing a liquid refrigerant;
    an external container surrounding the internal container and including a first external helmet and a second external helmet spaced apart from each other;
    a first sensor-mounted helmet surrounding the first external helmet between the external container and the internal container;
    a second sensor-mounted helmet surrounding the second external helmet between the external container and the internal container;
    a plurality of first SQUID sensor modules on the first sensor-mounted helmet, each comprising a first SQUID sensor and a first pick-up coil; and
    a plurality of second SQUID sensor modules on the second sensor-mounted helmet, each comprising a second SQUID sensor and a second pick-up coil,
    wherein a space between the external container and the internal container is in a vacuum state.

2. The dual-helmet magnetoencephalography measuring apparatus as set forth in claim 1, wherein the external container has a T form, including a first branch and a second branch branching off from a cylindrical external container body,
    the first external helmet and the second external helmet are coupled to the first branch and the second branch, respectively, and
    the first external helmet and the second external helmet face each other and have different sizes.

3. The dual-helmet magnetoencephalography measuring apparatus as set forth in claim 2, further comprising:
    a C-shaped external container support portion supporting lower surfaces of the first branch and the second branch; and
    a rotational motion unit coupled to the C-shaped external container support portion to provide a rotational motion to the external container.

4. The dual-helmet magnetoencephalography measuring apparatus as set forth in claim 3, further comprising:
    a vacuum-sealing portion in a through-hole in the lower surface of each of the first and second branches to seal signal lines, the vacuum-sealing portion being inside the C-shaped external container support portion; and
    a signal line connection box below the C-shaped external container support portion and connecting the signal lines to each other, and
    wherein the rotational motion unit further comprises:
        an upper base box surrounding the signal line connection box;
        a lower base box below the upper base box; and
        a bearing portion between the upper base box and the lower base box to provide a rotational motion to the upper base box.

5. The dual-helmet magnetoencephalography measuring apparatus as set forth in claim 4, further comprising:
    a handle coupled to an external side of the upper base box.

6. The dual-helmet magnetoencephalography measuring apparatus as set forth in claim 3, wherein the first external helmet includes a coupled portion with a first long groove,
    the first external helmet is coupled to one end of the first branch while rotating along the first long groove in an aligned state,
    the second external helmet includes a coupled portion with a second long groove, and
    the second external helmet is coupled to one end of the second branch while rotating along the second long groove in an aligned state.

7. The dual-helmet magnetoencephalography measuring apparatus as set forth in claim 1, further comprising:
    a rotational motion unit rotating the internal container and the external container about a central axis of the rotational motion unit.

8. The dual-helmet magnetoencephalography measuring apparatus as set forth in claim 1, wherein the internal container comprises:
    a neck portion,
    a baffle insert in the neck portion; and
    an internal body portion having an increased diameter as compared with the neck portion, and
    wherein the neck portion has a double-wall structure including an internal cylinder and an external cylinder surrounding the internal cylinder.

9. The dual-helmet magnetoencephalography measuring apparatus as set forth in claim 8, wherein the neck portion further comprises a heat shielding layer between the internal cylinder and the external cylinder.

10. The dual-helmet magnetoencephalography measuring apparatus as set forth in claim 8, wherein the internal cylinder further comprises a plurality of ring projections protruding outwardly from the internal cylinder,
    the dual-helmet magnetoencephalography measuring apparatus further comprises thermal anchors coupled to respective ones of the ring projections, and
    the ring projections are spaced apart from each other.

11. The dual-helmet magnetoencephalography measuring apparatus as set forth in claim 10, wherein an external circumferential surface of the ring projections and an internal circumferential surface of the thermal anchors are screw-coupled to each other.

12. The dual-helmet magnetoencephalography measuring apparatus as set forth in claim 11, wherein each of the thermal anchors comprises a cylindrical thermal anchor coupling portion and a disc-shaped thermal anchor body portion on an external circumferential surface of the cylindrical thermal anchor coupling portion, and an internal circumferential surface of the cylindrical thermal anchor coupling portion is screw-coupled to the external circumferential surface of a respective one of the ring projections.

13. The dual-helmet magnetoencephalography measuring apparatus as set forth in claim 10, wherein the external cylinder is separated with the ring projection therebetween.

14. The dual-helmet magnetoencephalography measuring apparatus as set forth in claim 1, wherein the internal container comprises:
a neck portion,
a baffle insert in the neck portion; and
a body portion having a diameter increased as compared to the neck portion,
wherein the dual-helmet magnetoencephalography measuring apparatus further comprises:
a refrigerant exhaust tube at the baffle insert and exhausting an evaporated refrigerant;
a liquid refrigerant injection tube at the baffle insert and injecting a liquid refrigerant; and
a condenser connected to the refrigerant exhaust tube and the liquid refrigerant injection tube and condensing the evaporated refrigerant, and the liquid refrigerant injection tube has a coaxial structure in the refrigerant exhaust tube.

15. The dual-helmet magnetoencephalography measuring apparatus as set forth in claim 14, wherein each of the refrigerant exhaust tube and the liquid refrigerant injection tube comprises a dual tube including an internal tube and an external tube.

16. The dual-helmet magnetoencephalography measuring apparatus as set forth in claim 1, wherein the internal container comprises:
a neck portion,
a baffle insert in the neck portion; and
a first body portion having an increased diameter as compared with the neck portion;
a second body portion having an increased diameter as compared with the first body portion; and
a third body portion having a decreased diameter as compared with the second body portion.

17. The dual-helmet magnetoencephalography measuring apparatus as set forth in claim 16, further comprising:
a pair of first support portions coupled to an interface between the neck portion and the first body portion and respectively extending in a direction of the first external helmet and a direction of the second external helmet;
a pair of second support portions coupled to an interface between the first body portion and the second body portion and respectively extending in the direction of the first external helmet and the direction of the second external helmet;
a pair of third support portions coupled to an interface between the second body portion and the third body portion and respectively extending in the direction of the first external helmet and the direction of the second external helmet;
a first fixing ring coupled to the first, second, and third support portions in the direction of the first external helmet;
a second fixing ring coupled to the first, second, and third support portions in the direction of the second external helmet;
a first auxiliary fixing part connecting the first fixing ring and the first sensor-mounted helmet; and
a second auxiliary fixing part connecting the second fixing ring and the second sensor-mounted helmet.

18. The dual-helmet magnetoencephalography measuring apparatus as set forth in claim 17, wherein each of the first, second, and third support portions comprises a plurality of arc long grooves, and
a coupling member is in each of the arc long grooves to be coupled to the internal container.

19. The dual-helmet magnetoencephalography measuring apparatus as set forth in claim 1, wherein the first sensor-mounted helmet comprises:
a helmet body having an open region for securing a view;
a lower brim along an edge of a lower surface of the helmet body;
an upper brim providing a brim in the open region of the helmet body;
a helmet fixing ring having a ring shape at a predetermined interval from the lower brim and continuously connected to the upper brim; and
a plurality of connection pillars vertically connecting the lower brim and the upper brim to each other.

20. The dual-helmet magnetoencephalography measuring apparatus as set forth in claim 19, further comprising:
a first auxiliary thermal anchor on a lower surface of each of the upper brim and the lower brim of the first sensor-mounted helmet;
a first internal 4K heat shielding portion in thermal contact with the first auxiliary thermal anchor and on an internal side surface of the first sensor-mounted helmet; and
a first external 4K heat shielding portion in thermal contact with the first auxiliary thermal anchor and on an external side surface of the first sensor-mounted helmet,
wherein the first auxiliary thermal anchor, the first internal 4K heat shielding portion, and the first external 4K heat shielding portion are in thermal contact with a main thermal anchor by a litz wire.

21. The dual-helmet magnetoencephalography measuring apparatus as set forth in claim 1, wherein each of the plurality of first SQUID sensor modules is in thermal contact with a main thermal anchor on a lower surface of the internal container through a first litz wire, and
each of the plurality of second SQUID sensor modules is in thermal contact with the main thermal anchor on the lower surface of the internal container through a second litz wire.

22. The dual-helmet magnetoencephalography measuring apparatus as set forth in claim 21, wherein the main thermal anchor comprises:
a first heat transfer unit comprising oxygen-free copper, a first disc, a first upper projection protruding from a central axis of the first disc to an upper surface of the first disc, and a first lower projection protruding from the central axis of the first disc to a lower surface of the first disc;
a second heat transfer unit comprising oxygen-free copper, a second disc, a second upper projection protruding from a central axis of the second disc to an upper surface of the second disc, and a second lower projection protruding from the central axis of the second disc to a lower surface of the second disc;
a third heat transfer unit comprising oxygen-free copper, a third disc, a third upper projection protruding from a central axis of the third disc to an upper surface of the third disc, and a third lower projection protruding from the central axis of the third disc to a lower surface of the third disc;

a fourth heat transfer unit comprising oxygen-free copper, a fourth disc, a fourth upper projection protruding from a central axis of the fourth disc to an upper surface of the fourth disc, and a fourth lower projection protruding from the central axis of the fourth disc to a lower surface of the fourth disc;

a fifth heat transfer unit, comprising oxygen-free copper, coupled to the fourth heat transfer unit and having a strip shape;

a first thermal expansion control unit comprising an insulating material, between the first disc of the first heat transfer unit and the second disc of the second heat transfer; and a second thermal expansion control unit comprising an insulating material, between the third disc of the third heat transfer unit and the fourth disc of the fourth heat transfer unit, wherein the second upper projection of the second heat transfer unit includes a groove for coupling to the first lower projection of the first heat transfer unit, the second lower projection of the second heat transfer unit includes a groove for coupling to the third upper projection of the third heat transfer unit, and the third lower projection of the third heat transfer unit includes a groove for coupling to the fourth upper projection of the fourth heat transfer unit.

23. The dual-helmet magnetoencephalography measuring apparatus as set forth in claim 22, wherein the first thermal expansion control unit comprises:

a first insulating body portion having a same diameter as a first diameter of the first disc;

a second insulating body portion in a lower surface of the internal container and having a second diameter greater than the first diameter; and a third insulating body portion having a third diameter smaller than the second diameter, wherein the third insulating body portion surrounds an external circumferential surface of the second disc.

24. The dual-helmet magnetoencephalography measuring apparatus as set forth in claim 1, wherein the first SQUID sensor modules are cooled by a plurality of litz wires, some of the plurality of litz wires are connected to ones of the first SQUID sensor modules, and a remainder of the plurality of litz wires are in thermal contact with a main thermal anchor.

25. The dual-helmet magnetoencephalography measuring apparatus as set forth in claim 24, wherein the plurality of litz wires comprises six litz wires, two of the six litz wires are in thermal contact with the main thermal anchor, and a remaining four of the six litz wires are connected to the first SQUID sensor modules.

26. The dual-helmet magnetoencephalography measuring apparatus as set forth in claim 25, wherein the four litz wires extend from corresponding ones of the first SQUID sensor modules.

27. The dual-helmet magnetoencephalography measuring apparatus as set forth in claim 24, wherein the some of the plurality of litz wires extend from corresponding ones of the first SQUID sensor modules.

28. The dual-helmet magnetoencephalography measuring apparatus as set forth in claim 1, wherein the internal container comprises a neck portion and a baffle insert in the neck portion, and the neck portion has a double-wall structure, washer-shaped first to third thermal anchors, vertically spaced apart from each other, are on an external side of the neck portion, the first thermal anchor is connected to a 120K heat shielding layer, the second thermal anchor is connected to an 80K heat shielding layer, and the third thermal anchor is connected to a 40K heat shielding layer.

29. The dual-helmet magnetoencephalography measuring apparatus as set forth in claim 28, wherein the 40K heat shielding layer surrounds the first sensor-mounted helmet and the second sensor-mounted helmet.

30. The dual-helmet magnetoencephalography measuring apparatus as set forth in claim 1, wherein each of the first SQUID sensor modules is at least partially in a through-hole in the first sensor-mounted helmet, each of the first SQUID sensor modules comprises a plurality of holes, and litz wires are in respective ones of the plurality of holes to cool a SQUID sensor.

31. The dual-helmet magnetoencephalography measuring apparatus as set forth in claim 30, wherein the SQUID sensor is in a corresponding one of the first SQUID sensor modules.

32. The dual-helmet magnetoencephalography measuring apparatus as set forth in claim 1, wherein the first and second sensor-mounted helmets have different sizes, one of the first and second sensor-mounted helmets is configured to cover a head of a child, and the other of the first and second sensor-mounted helmets is configured to cover a head of an adult.

* * * * *